(12) United States Patent
Chapman et al.

(10) Patent No.: US 7,297,516 B2
(45) Date of Patent: Nov. 20, 2007

(54) RECOMBINANT PEPTIDE

(75) Inventors: John William Chapman, Rotterdam (NL); Wouter Musters, Maassluis (NL); Pieter Dirk van Wassenaar, Maassluis (NL)

(73) Assignee: Good Humor - Breyer Ice Cream, division of Conopco, Inc., Green Bay, WI (US)

( * ) Notice: Subject to any disclaimer, the term of this patent is extended or adjusted under 35 U.S.C. 154(b) by 204 days.

(21) Appl. No.: 10/934,009

(22) Filed: Sep. 3, 2004

(65) Prior Publication Data

US 2005/0205833 A1    Sep. 22, 2005

Related U.S. Application Data

(62) Division of application No. 08/673,876, filed on Jul. 2, 1996, now Pat. No. 6,914,043.

(30) Foreign Application Priority Data

Jul. 5, 1995 (EP) .................................. 95201842
Oct. 10, 1995 (EP) .................................. 95202732

(51) Int. Cl.
    *C12P 21/06* (2006.01)
    *C07H 17/00* (2006.01)
    *C07K 14/00* (2006.01)
(52) U.S. Cl. ..................... 435/69.1; 536/23.1; 530/350
(58) Field of Classification Search ............... 435/69.1; 536/23.1; 530/300
See application file for complete search history.

*Primary Examiner*—Karen Cochrane Carlson
(74) *Attorney, Agent, or Firm*—Gerard J. McGowan, Jr.

(57) ABSTRACT

Use of a polypeptide or protein with amino acid sequence corresponding substantially to AFP-type III HPLC 12 as additive in a product for improvement of said product, said improvement residing in improved properties of modification of ice crystal growth processes influencing size and shape characteristics of ice in particular in regrowth thereby e.g. minimising potential freezing damage e.g. by preventing or inhibiting ice recrystallisation of the product upon freezing, said use occurring in a manner known per se for anti freeze peptides to obtain higher specific modification activity in particular antifreeze activity than obtainable with the same amount of Winter Flounder AFP.

9 Claims, 18 Drawing Sheets

FIG 1

Figure 4:
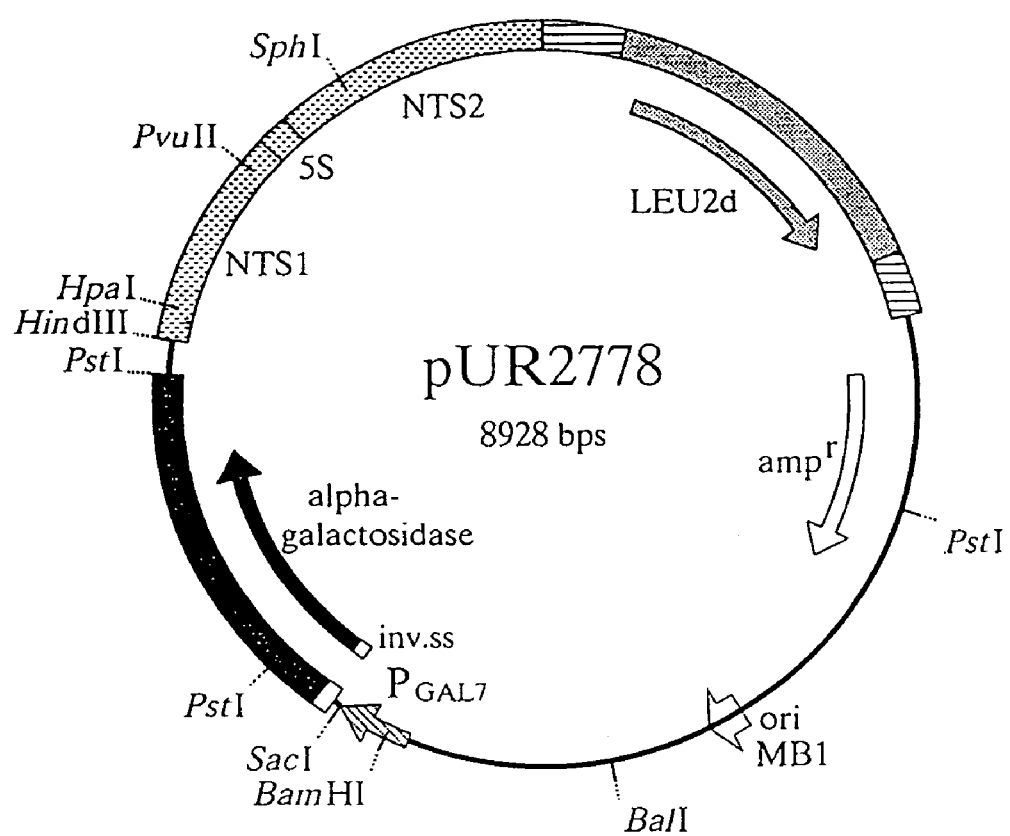

```
                    invafp1                              invafp2
5'   GCCAAAATATCTGCTAGCCAATCTGTTGTTGCTACTCAATTGATTCCAATGAATAC
3'ACGTCGGTTTTATAGACGATCGGTTAGACAACAACGATGAGTTAACTAAGGTTACTTATG
         invafp7                                  invafp8
                                  invafp3
TGCTTTGACTCCAGTTATGATGGAAGGTAAAGTTACTAATCCAATTGGTATTCCATTTGC
ACGAAACTGAGGTCAATACTACCTTCCATTTCAATGATTAGGTTAACCATAAGGTAAACG
                          invafp9
         invafp4                                    invafp5
TGAAATGTCTCAAATTGTTGGTAAACAAGTTAATACTCCAGTTGCTAAAGGTCAAACTAT
ACTTTACAGAGTTTAACAACCATTTGTTCAATTATGAGGTCAACGATTTCCAGTTTGATA
     invafp10                      invafp6            invafp11
TATGCCAAATATGGTTAAAACATATGCTGCTTAAGCTTG    3'
ATACGGTTTATACCAATTTTGTATACGACGAATTCGAACCTAG  5'
                     invafp12
```

Figure 2. Synthetic gene encoding AFP-III HPLC1.

FIG 3
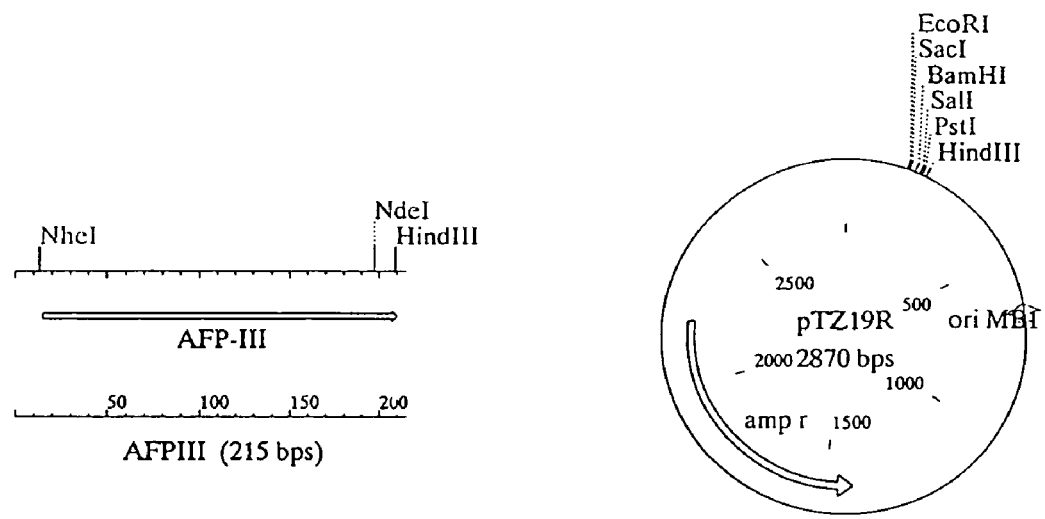
Cut
PstI/HindIII
And Ligate With
Synthetic
AFP-III Gene
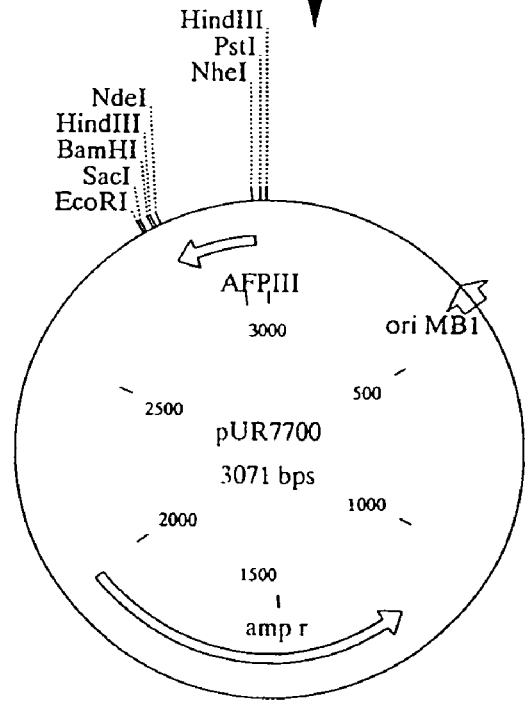

FIG. 5
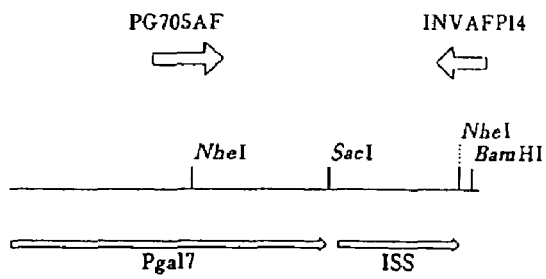
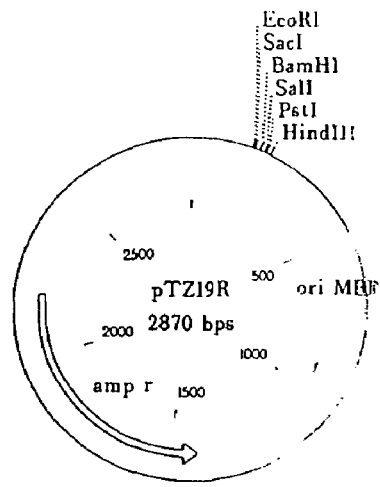
Cut with SacI/BamHI and ligate the 88 bp
fragment from the PCR product with the
vector fragment from pTZ19
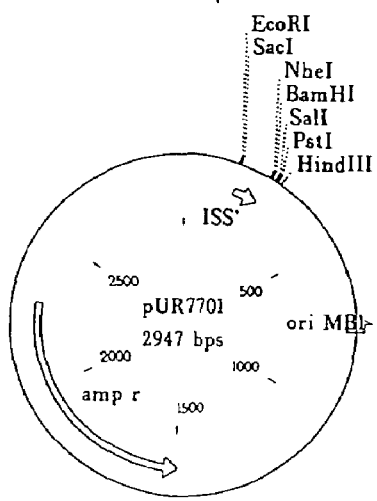

FIG 6
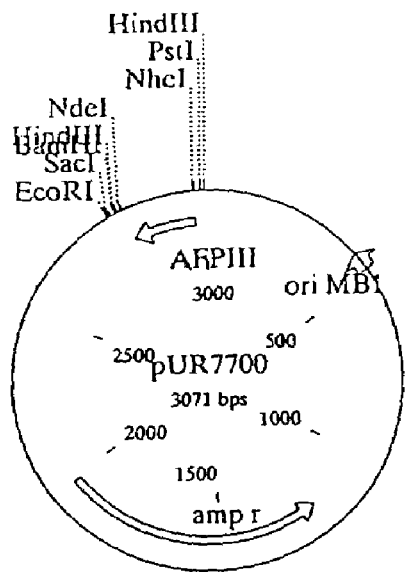
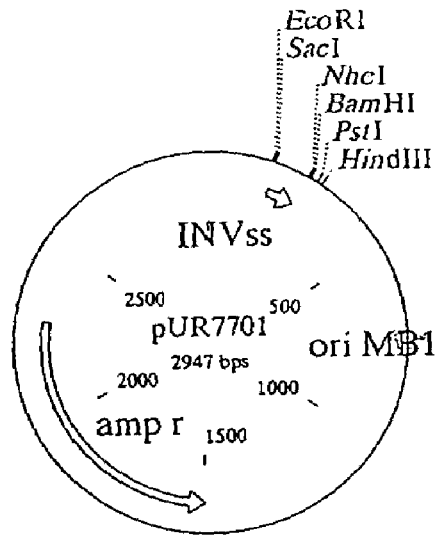
Cut with HindIII/NheI and ligate the 196 bp
fragment from pUR7700 with the 2991 bp
fragment from pUR7701
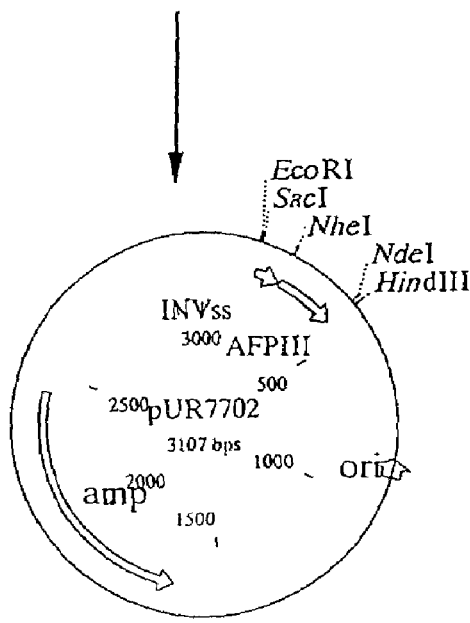

FIG 7
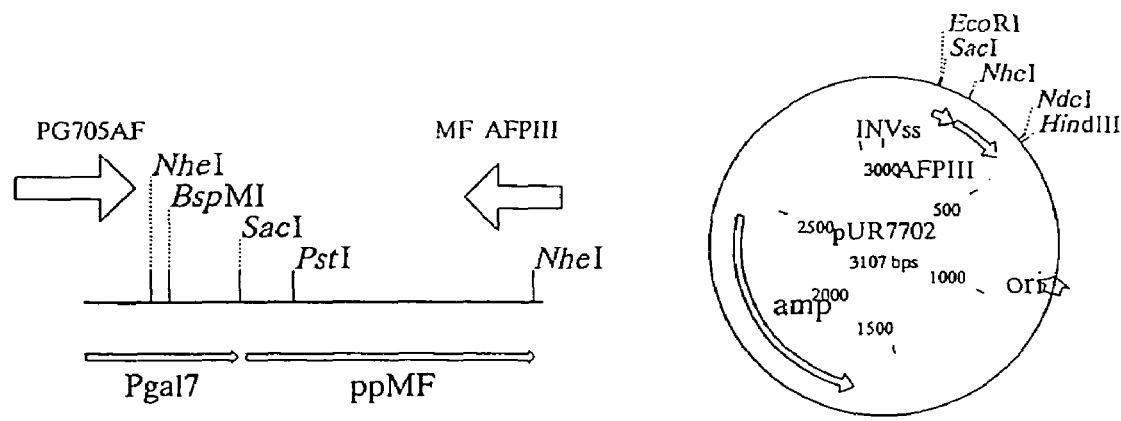
Cut with NheI/SacI and ligate the 292 bp
fragment from the PCR fragment with the
3025 bp fragment from pUR7702
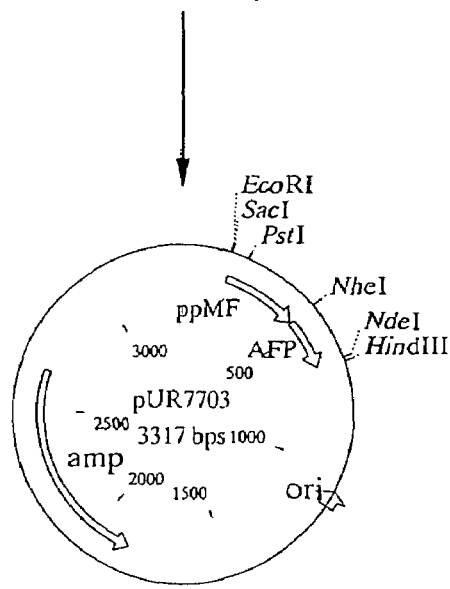

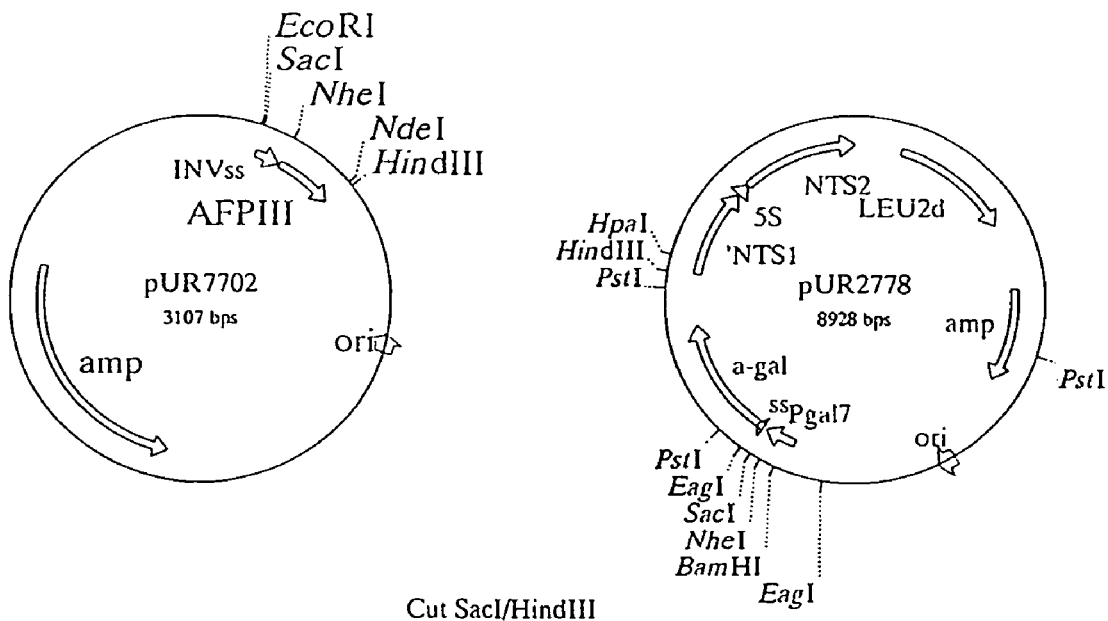
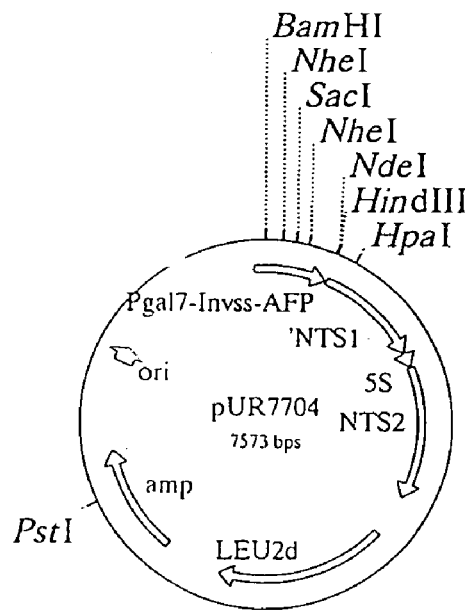
FIG 8

FIG 9
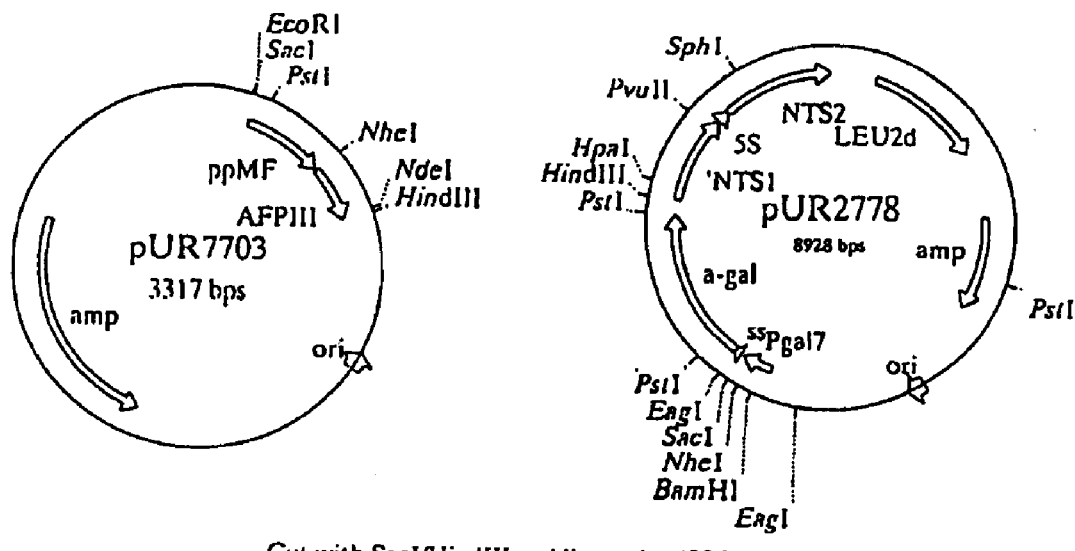
Cut with SacI/HindIII and ligate the 488 bp
fragment from pUR7703 with the 7295 bp
fragment from pUR2778
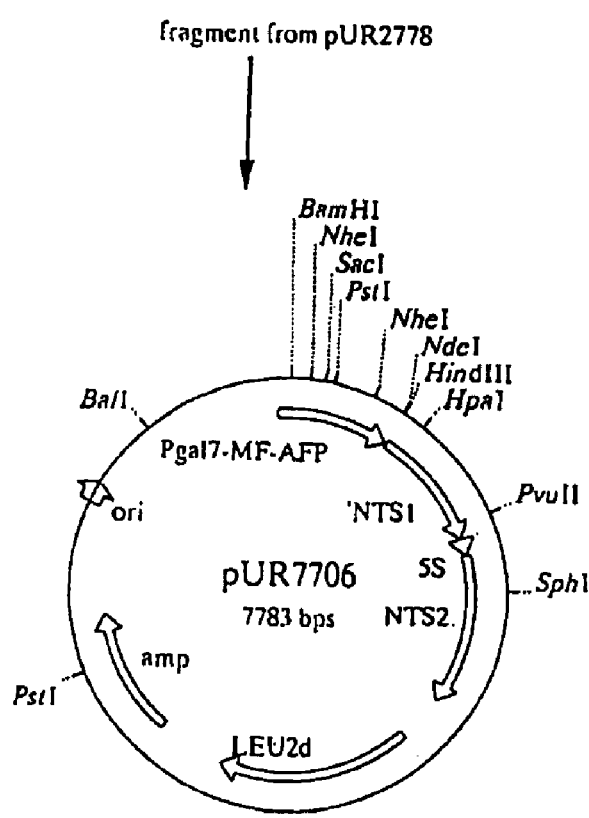

Figure 10 The elution pattern of ocean pout antifreeze peptides from a Mono S column.
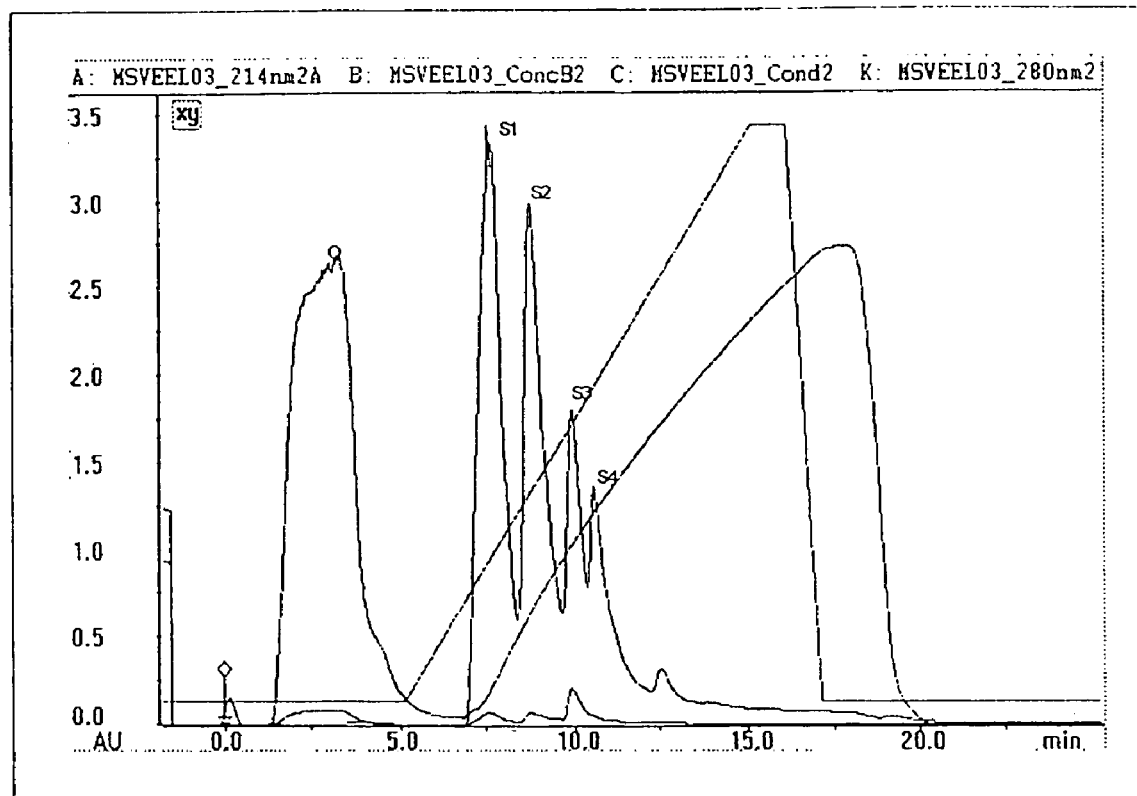

Figure 11 Chromatogram of antifreeze peptides separated by reversed phase HPLC.
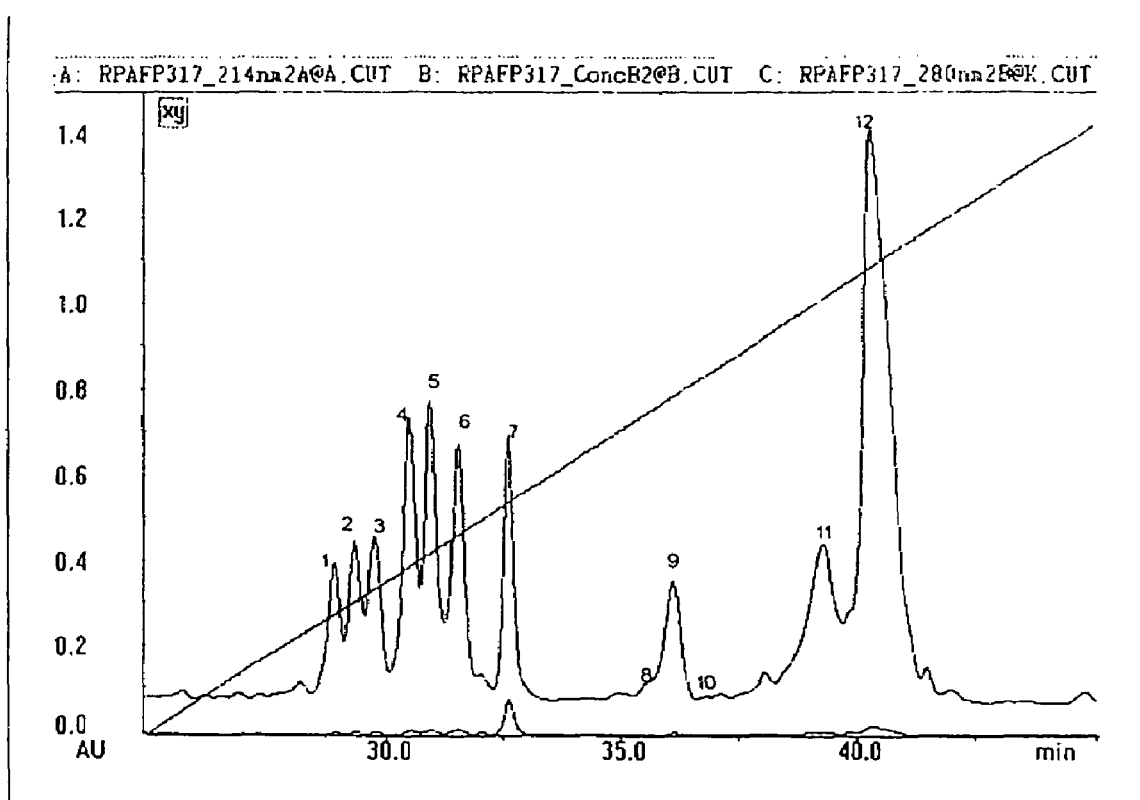

Figure 12 Chromatogram of Mono S S1 antifreeze peptides separated by reversed phase HPLC.
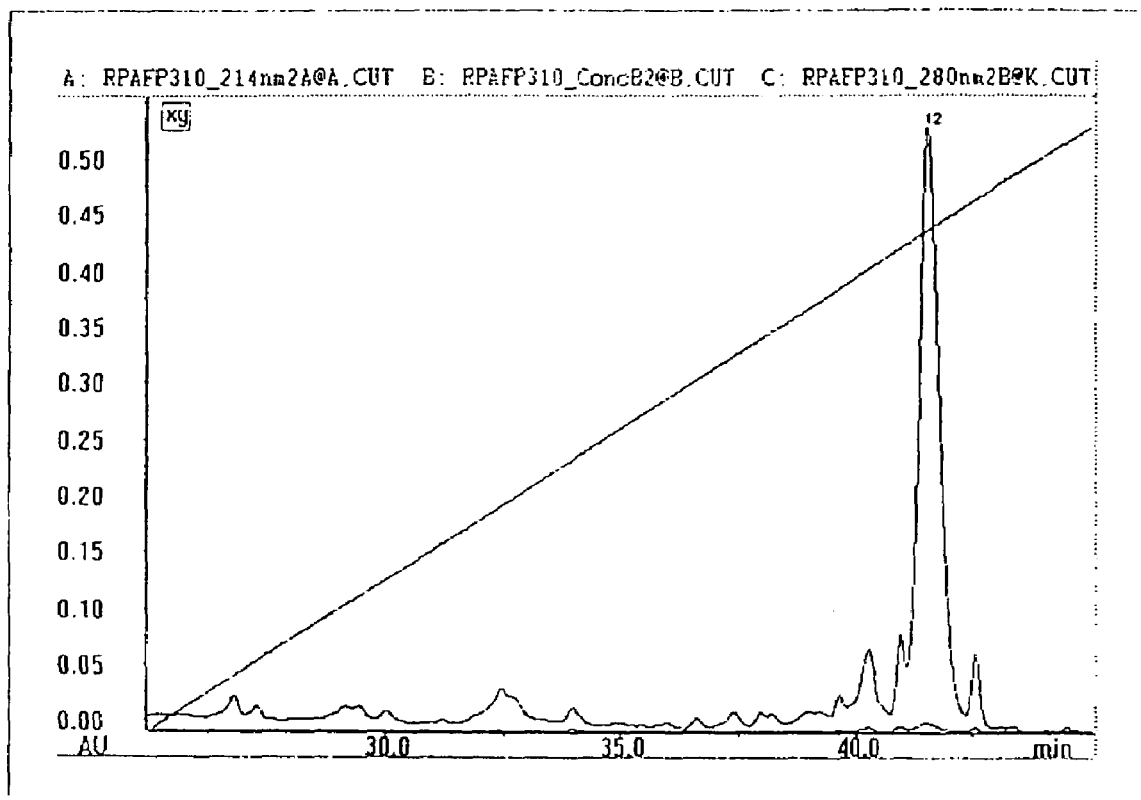

Figure 13 Chromatogram of Mono S S2 antifreeze peptides separated by reversed phase HPLC.
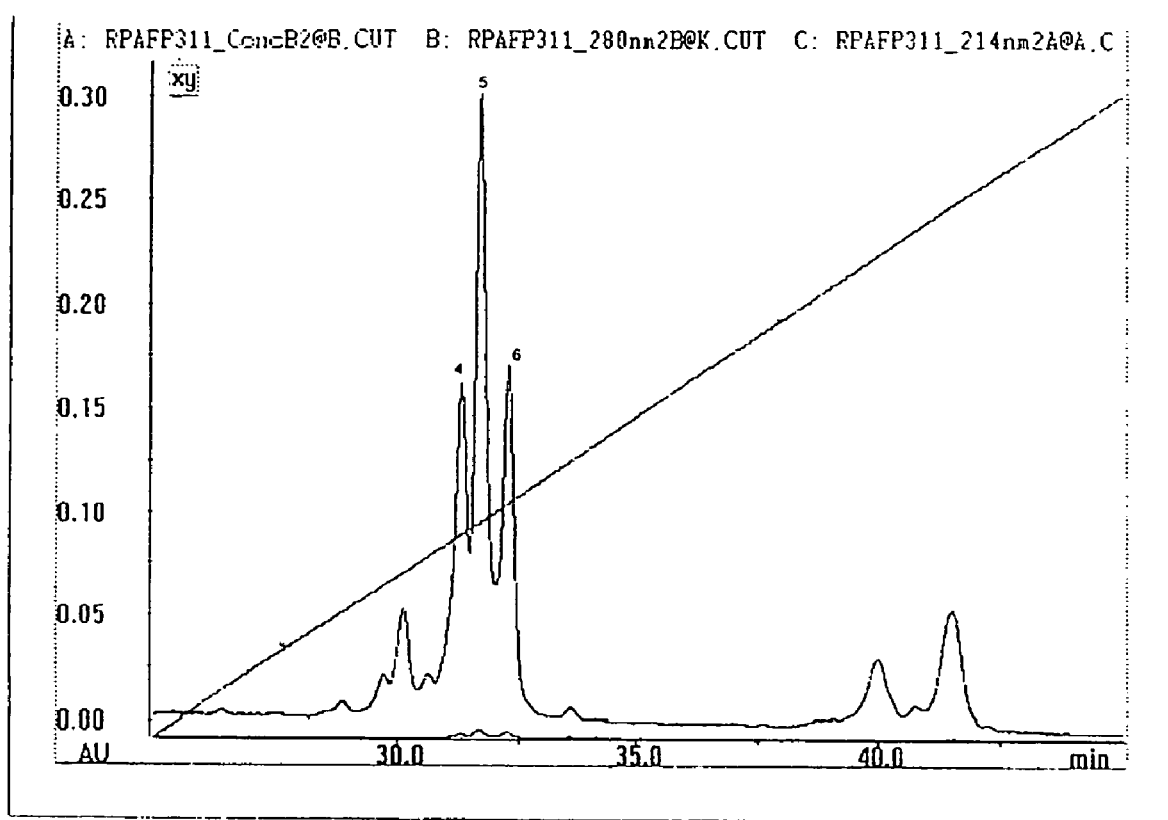

Figure 14. Chromatogram of Mono S S3 antifreeze peptides separated by reversed phase HPLC.
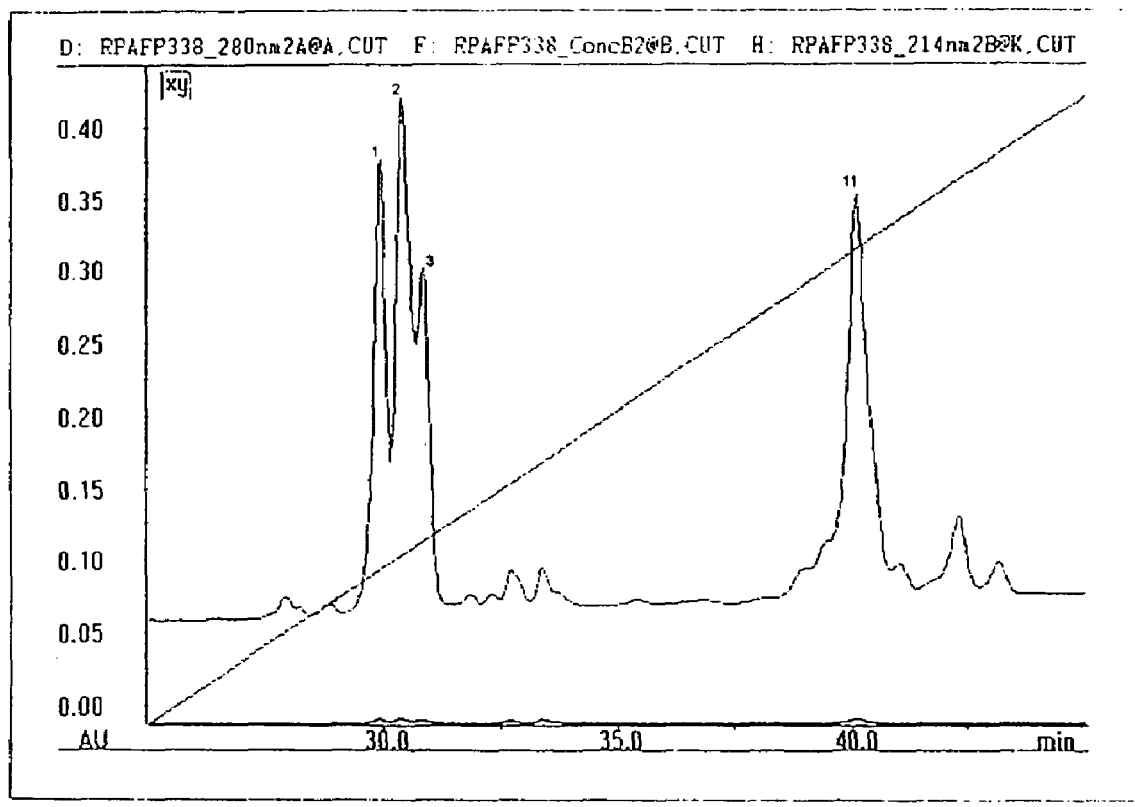

Figure 15 Chromatogram of Mono S S4 antifreeze peptides separated by reversed phase HPLC.
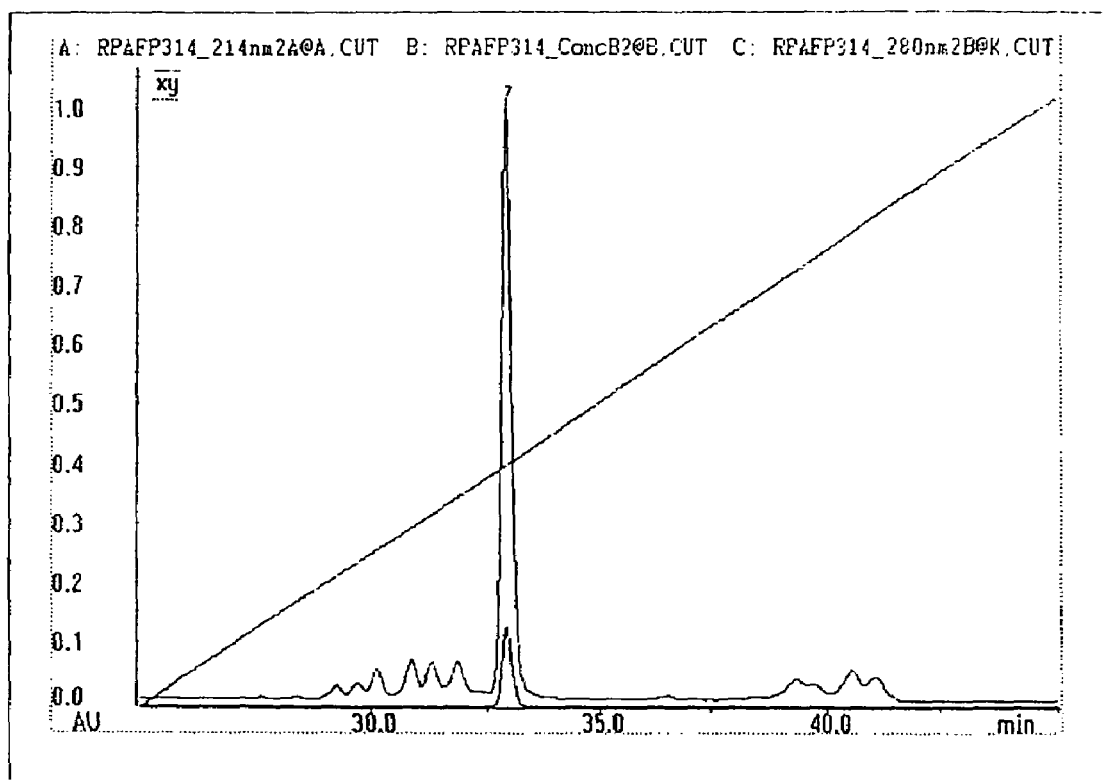

Figure 16 Chromatogram of Mono S S1 antifreeze peptides separated by reversed phase HPLC.
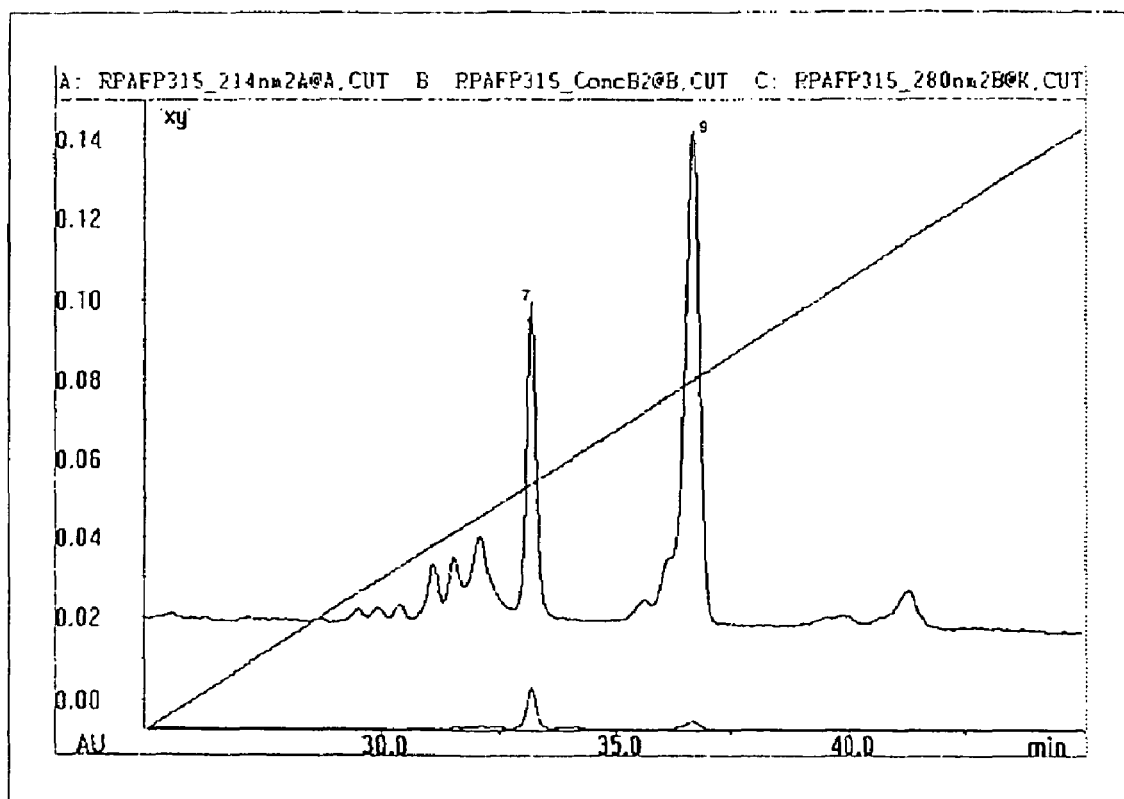

```
Sac I    <        HPLC12.1          ><        HPLC12.2        ><
  1  CATCACACAAACAAACAAAACAAAATGATGCTTTTGCAAGCCTTCCTTTTCCTTTTGGCTGGTTTTGCAGCCAAAATATCTGCTA   90
  1  ----------+---------+----------+---------+----------+---------+----------+---------+  90
     TCGAGTAGTGTGTTTGTTTGTTTTGTTTTACTACGAAACGTTCGGAAGGAAAAGGAAAACCGACCAAAACGTCGGTTTTATAGACGAT
       H  H  T  N  K  Q  N  K  M  M  L  L  Q  A  F  L  F  L  L  A  G  F  A  A  K  I  S  A
     <    HPLC12.8         ><    HPLC12.9              ><       HPLC12.10

HPLC12.3              ><        HPLC12.4                           ><
 91  ATCAAGCCTCTGTTGTTGCTAATCAATTGATTCCAATAAATACTGCTTTGACTCTAGTTATGATGAGAAGTGAAGTTGTTACTCCAGTTG  180
 91  ----------+---------+----------+---------+----------+---------+----------+---------+     180
     TAGTTCGGAGACAACAACGATTAGTTAACTAAGGTTATTTATGACGAAACTGAGATCAATACTACTCTTCACTTCAACAATGAGGTCAAC
       N  Q  A  S  V  V  A  N  Q  L  I  P  I  N  T  A  L  T  L  V  M  M  R  S  E  V  V  T  P  V
              ><      HPLC12.11                              ><      HPLC12.12

HPLC12.5           ><        HPLC12.6                     ><
181  GTATTCCAGCTGAAGATATCCCTAGACTTGTTAGTATGCAAGTTAATAGAGCAGTTCCTTTGGGTACCACTCTTATGCCAGATATGGTTA  270
181  ----------+---------+----------+---------+----------+---------+----------+---------+      270
     CATAAGGTCGACTTCTATAGGGATCTGAACAATCATACGTTCAATTATCTCGTCAAGGAAACCCATGGTGAGAATACGGTCTATACCAAT
       G  I  P  A  E  D  I  P  R  L  V  S  M  Q  V  N  R  A  V  P  L  G  T  T  L  M  P  D  M  V
              ><    HPLC12.13                    ><      HPLC12.14

HPLC12.7          >
271  AAGGTTATCCTCCTGCTTAGTCTTCA   303
271  ----------+---------+-----   303
     TTCCAATAGGAGGACGAATCAGAAGTTCGA
       K  G  Y  P  P  A  *  S  S
     ><    HPLC12.15          >  HindIII
```

Figure 17 Synthetic gene encoding type III AFP HPLC12 invertase signal sequence fusion protein.

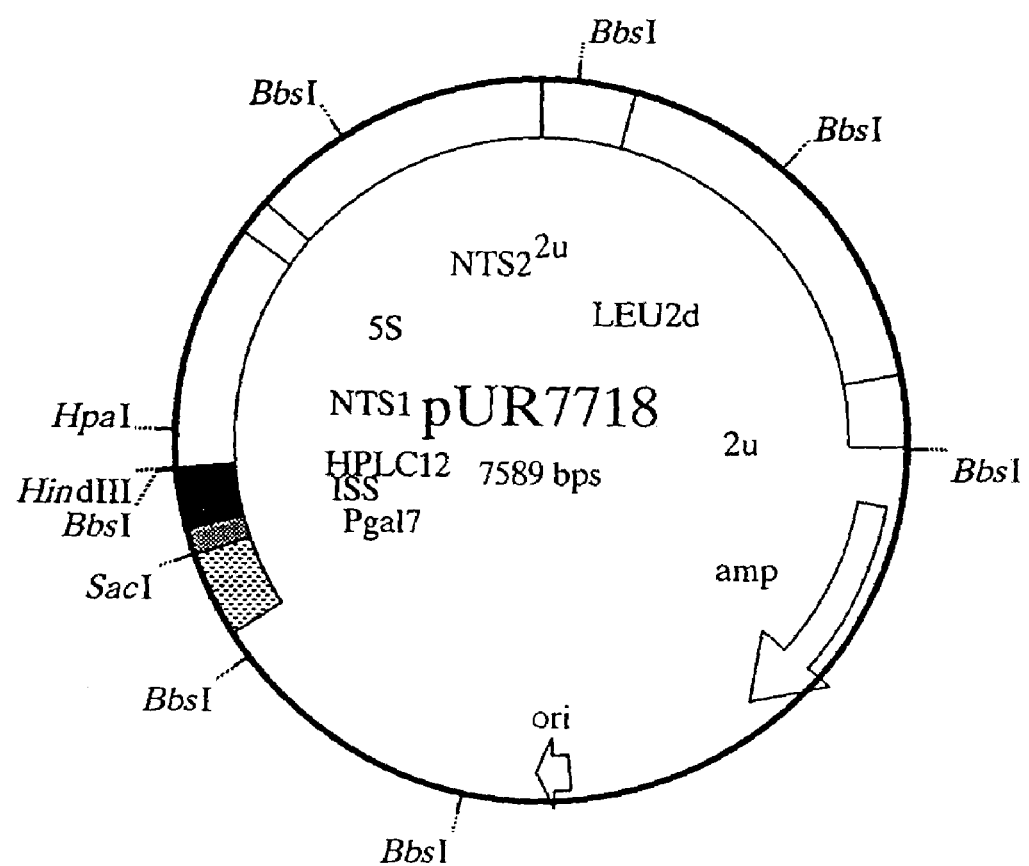
F-18

RECOMBINANT PEPTIDE

This application is a divisional of U.S. Ser. No. 08/673,876, filed Jul. 2, 1996, now U.S. Pat. No. 6,914,043, which claims benefit of foreign European applications 95201842.2, filed Jul. 5, 1995, and 95202732.4, filed Oct. 10, 1995.

1. INTRODUCTION

The blood of polar fish is protected from freezing by the presence of antifreeze peptides. These antifreeze peptides can be classified into four types according to their structures (Davies and Hew, 1990). The type I AFP's are alanine rich with regularly spaced threonine and asparagine residues and have an α-helical conformation. Type-II AFP's have a characteristic high (8%) cysteine content. Type-III AFP's are small (approximately 64 amino acids long) globular peptides. The final group, the antifreeze glycoproteins have a repeated tripeptide motif to which is attached a specific disaccharide. All of these peptides share the property of non colligative freezing point depression and inhibition of ice crystal growth. These features may find application in altering the ice crystal state of frozen products. As purification of these peptides from fish blood is unlikely ever to be an economically viable process, a method was sought for the bulk production of AFP's using modern biotechnology.

Early work on the production of antifreeze peptides in microorganisms concentrated on the expression of type-I AFP's in both yeast and *Escherichia coli* (Warren et al, 1993, McKown et al, 1991). As *E. coli* has the capacity to produce toxins, this bacterium is not generally regarded as safe (GRAS) which poses problems for its use in the production of AFP's destined for application in the food industry.

Yeast strains like *Saccharomyces cerevisiae* are known that are considered GRAS organisms and, unlike *E. coli*, have the capacity to secrete heterologous proteins into the growth medium which facilitates downstream processing of the product. Yeast is therefore an attractive host organism for the production of a variety of heterologous proteins (Romanos et al, 1992).

The first reports of AFP production in yeast relate to the intracellular accumulation of a fusion of a synthetic type-I AFP with a truncated *Staphylococcus aureus* protein A (Warren et al, 1993). It was claimed that this peptide protected the yeast against the deleterious effects of freezing. No extracellular production of type-I AFP as such is described. Nothing is mentioned with regard to other types of AFP.

In this laboratory, yeast transformants carrying an expression vector containing a synthetic gene for a natural Winter Flounder type-I AFP (HPLC6) have been constructed (Driedonks et al, 1995) and this is described in applicant's PCT application WO 94/03617 now abandoned. The secretion of active monomer AFP by these yeasts was not demonstrable. The only way to obtain significant ice recrystallisation inhibition activity was to express multimers of the type-I AFP designed to allow their subsequent processing by an endogenous yeast protease to yield active monomers (Driedonks et al, 1995). This approach, although ultimately allowing for the production of active type-I AFP, resulted in the secretion of partially processed heterogeneous forms of the multimeric AFP. The subsequent treatment to obtain active peptide as a monomer was considered unacceptable for industrial production purposes. Besides the extra effort and costs such addition could also lead to problems in obtaining permission for application in foodstuffs. This is firstly due to the use of chemicals to obtain active monomers and secondly due to the expression of non native sequences.

It thus appeared impossible to use a food grade organism to express and secrete active monomeric AFP in a simple and efficient manner providing an industrially acceptable process applicable in food production.

In an attempt to overcome the problems posed by expressing type-I AFP in yeast, we attempted to express type-III AFP's from Ocean Pout in yeast. The type-III AFP's are small globular proteins and we considered that for this reason they could be more suitable for expression in yeast than the a helical type I AFP's.

The type-III AFP's are found in the blood of polar fish such as Ocean Pout (*Macrozoarces americanus*) and Wolffish (Davies and Hew, 1990). Fractionation of the blood of Ocean Pout has been described as revealing the presence of at least 12 different varieties of type-III AFP (FIG. 1, Hew et al, 1984, Davies and Hew, 1990). These peptides are highly homologous, sharing at least 60% amino acid identity and in vitro mutagenesis has demonstrated a cluster of surface residues common to all variants of Ocean Pout AFP which are required for the binding to ice (Chao et al, 1994). The negative charge of Glutamic acid (Glu) at positions 23 and 36 appears to be involved in the thermal stability and thermal hysteretic activity of the polypeptide (Li et al, 1991). Asparagine (Asn) at position 14, Threonine (Thr) at 18 and Glutamine (Gln) at 44, the next three conserved amino acids, also appear to be key residues in the ice binding activity of AFP-III (Chao et al, 1994).

We managed to express the HPLC-1 variant of Ocean Pout type-III AFP in yeast, but were not able to obtain secretion of a sufficiently active monomer of type-III AFP. This obviously did not solve the above mentioned problems.

In addition we determined that the type-III AFP HPLC-1 produced by the yeast exhibited an unexpectedly low specific activity when compared to the AFP preparation isolated from Ocean Pout blood. This low activity could possibly be due to incorrect folding of the peptide or due to an inherently lower specific activity of the HPLC-1 variant. It certainly did not look promising to continue this line of research for producing more active AFP's than those found in the Winter Flounder.

We also fractionated AFP derived from Ocean Pout blood into the various HPLC fractions and analyzed their recrystallisation activity in order to ascertain which fraction other than HPLC-1 could potentially be useful for our desired application. HPLC 12 appeared to be the only fraction of the 12 AFP-type III fractions active in recrystallisation inhibition at the concentrations tested. Thus we determined HPLC-12 could be of interest if we could manage to overcome the problems in recombinant production thereof that had been found for AFP-type I and HPLC-1 of AFP-type III.

Quite unexpectedly in view of the above experiments with both type-I AFP and type-III AFP we subsequently found that yeast expression of nucleic acid encoding the amino acid sequence determined for type-III AFP HPLC-12 leads to a product that is expressed and secreted as a monomer and does not exhibit reduced activity. Thus an eminently suitable production process using recombinant DNA technology for producing pure active AFP was available.

What was in fact additionally discovered was that recombinant HPLC-12 secreted by yeast as a monomer as such can exhibit the high antifreeze peptide activity of a mixture of AFP isolated from Ocean Pout blood. This antifreeze activity is almost double that of Winter Flounder type-I AFP. In addition the product is thus more active in recrystallisation assays and much more suitable for the desired applications than other AFP's.

The amino acid composition, sequences and nucleic acid sequences of various type-III AFP's occurring in nature were already known. Davies and Hew (1990) give a review thereof and refer to articles of Li et al from 1985 and Hew et al. from 1988 for sequences of HPLC-1,4,5-7,9, 11 and 12 as determined for Ocean Pout on the basis of cDNA clones of genomic DNA of fish in phages. In Protein Science in 1994 Chao, H et al. describe how an isoform of type-III AFP HPLC-12 is synthetically synthesized and expressed in E. coli for two dimensional NMR studies to help understand the structure/function relationships in antifreeze proteins and to define the motifs for ice binding. The nucleic acid is subsequently mutated in order to produce mutant type-III AFP polypeptide, said mutants being proline mutants. The thermal hysteresis value of non mutated recombinant HPLC-12 was compared to AFP isolated from Ocean Pout i.e. type-III AFP. The activity profiles were described as being indistinguishable within the limits of standard errors. No comparison with other AFP types is mentioned. No indication of an abnormally high value of thermal hysteresis is given, in fact no value is given at all. Nothing is stated with regard to any effect on recrystallisation properties. We hereby point out that thermal hysteresis activities are not linked to recrystallisation properties. Thermal hysteresis values are indicative of binding strength and do not give a measure of antifreeze activity like a recrystallisation assay. Examples are known of proteins exhibiting high hysteresis values but no effect on recrystallisation and vice versa which illustrates the lack of correlation.

The high AFP activity of the recombinant HPLC-12 was totally unexpected in view of the results obtained for recombinant HPLC-1 and in view of what has been disclosed in publications concerned with AFP's. Values of the thermal hysteresis of type-III AFP fractions as obtained through Sephadex column fractionation of Ocean Pout type-III AFP's derived from blood are given in the Hew et al 1984 article in Table 1 as are values for Flounder AFP (=Type-I) and Sea Raven AFP (=Type-II). These values were derived for fractions derived from blood of the relevant species, not through recombinant DNA technology. There appeared to be only slight differences in the activities between the AFP's with the most active being QAE-A. QAE-A was one of 5 distinct variants which could be separated on a QAE Sephadex column and was subsequently shown to be derived from HPLC-12. However the differences are described as being so slight as to fall within the deviation due to measurement variations. The differences in thermal hysteresis values were clearly dismissed as being irrelevant by Hew et al themselves in the very same article. They state "Most of the Ocean Pout AFP exhibited thermal hysteresis comparable with that found for other known AFGP and AFP". In later literature no mention of thermal hysteresis values for the various types or comparisons between Type-I and Type-III are given. Nothing is taught or suggested regarding recrystallisation effects of the various fractions. Therefore, it was not to be expected that any single type-III AFP would exhibit a lot higher specific activity for ice crystal growth inhibition than Winter Flounder AFP. It had also not been disclosed or suggested that HPLC-12 exhibits a much higher activity than any type I-AFP peptide or other type-III AFP peptide.

To test whether the AFP activity of type-III HPLC-12 was higher we fractionated the Ocean Pout AFP preparation derived from blood via HPLC and we tested the individual peptide components for their ability to inhibit ice crystal growth. We determined that the HPLC-12 variant had the highest specific activity. The other components showed no detectable activity at a concentration equivalent to 100 mg fish type-III AFP per ml.

Thus we have found a method of preparing a pure food grade polypeptide exhibiting AFP activity almost double that of type-I AFP. Because it can be secreted as a monomer in contrast to Type-I AFP this makes it ideal for large scale production, requiring a lot less down stream processing than type-I AFP produced via recombinant technology. In addition the expression as a monomer means a product nearly identical to the naturally occurring peptide in Ocean Pout blood can be produced. Such a product will be more easily admitted for use in foodstuffs due to it's close resemblance to the naturally occurring AFP in the native food grade organism, the Ocean Pout.

The subject invention now allows us to produce for the first time on a large scale at low cost and great ease recombinant type-III AFP's of the HPLC-12 type which have an inherently higher specific activity than the Winter Flounder type-I AFP's. The type-III antifreeze peptides according to the invention are the most promising candidates for application in food products destined to be frozen such as ice cream and frozen dough and other frozen bakery products due to their high specific recrystallisation inhibiting activities.

An additional advantage lies in the fact that secretion of the expression product as active polypeptide, preferably as a monomer can now occur in situ in the food production process, thereby eliminating the requirement of addition of the AFP as such. It can now become possible to produce fermentation products using a yeast capable of secreting a polypeptide substantially corresponding to type-III AFP HPLC-12 in the fermentation process, whereby in situ production of polypeptide substantially corresponding to type-III AFP HPLC-12 occurs without requiring additional steps such as purification of the polypeptide and subsequent addition thereof in the food production process. Also development of plants, fruit or vegetables and transgenic animals or parts thereof with better freezing properties due to the in situ expression of a polypeptide substantially corresponding to type-III AFP HPLC-12 is now possible.

2. DETAILED DESCRIPTION OF THE INVENTION

The subject invention is directed at a process for preparing an improved product, the improvement residing in modification of ice crystal growth processes influencing size and shape characteristics of ice in particular in regrowth thereby e.g. minimising potential freezing damage e.g. by preventing or inhibiting ice recrystallisation of the product upon freezing, said process comprising addition of a polypeptide or protein with an amino acid sequence substantially corresponding to that of AFP-type III HPLC 12 exhibiting AFP activity higher than of AFP-type I from Winter Flounder to the non improved product or to an ingredient or mixture normally used in preparing the non improved product, said addition of recombinant polypeptide or protein occurring in an amount sufficient to affect ice crystal growth. The product can be a food product or a biological material. The biological material can for example be an animal organ or tissue or be plant material. In particular recombinant polypeptide can be added. Preferably the polypeptide will be of food grade status in order to provide the final product with food grade status. A process according to the invention wherein the product is a food product is preferred. A specific embodiment of a suitable polypeptide is a yeast AFP as illustrated in the Examples. Suitably a production process according to the invention directed at production of an improved product exhibiting improved freezing properties can comprise addition of an AFP obtained in a new polypeptide production process which also falls within the scope of the invention and is elucidated elsewhere in the description.

The term "a polypeptide or protein with an amino acid sequence substantially corresponding to that of AFP-type III HPLC 12" comprises an amino acid sequence equal to the amino acid sequence of HPLC-12 isolated from Ocean Pout and also comprises an amino acid sequence that differs by one or two amino acids from the known amino acid sequence but still encodes a polypeptide with the same AFP activity as the native protein. The mutations or differences may not be in amino acids known to be essential for activity of the polypeptide. Proline residues are preferably therefore not deleted or replaced. Preferably any differences in amino acid sequence are silent mutations, whereby the substitutions are conservative substitutions that do not alter the hydropathy profile of the polypeptide and thus presumably do not severely influence the polypeptide structure and the activity, i.e. an amino acid with a hydrophobic side chain is preferably only exchanged for another amino acid with a hydrophobic side chain and an amino acid with a hydrophillic side chain is only replaced by another amino acid with a hydrophillic side chain. The amino acid homology between HPLC-12 and HPLC-1 is less than 60%. An amino acid sequence exhibiting homology above 60% preferably more than 70% and most preferably more than 80% can be expected to be representative of a polypeptide exhibiting similar properties to HPLC-12 and thus is also considered substantially corresponding to HPLC-12. In addition the polypeptide encoded by the amino acid sequence should exhibit at least the AFP activity of AFP-type I from Winter Flounder and preferably at least the AFP activity of, native HPLC-12. The AFP activity can be determined by carrying out comparisons with recrystallisation assays using a series of dilutions of the polypeptide to be determined and equal amounts and dilutions of AFP-type I and/or native HPLC-12 as obtained from Ocean Pout blood. The manner in which such a recrystallisation assay can be carried out and evaluated is illustrated in the Examples. A polypeptide exhibiting any or a number of the above mentioned characteristics may be considered corresponding substantially to HPLC-12.

A process for preparing an improved product, the improvement residing in improved properties due to modification of ice crystal growth processes influencing size and shape characteristics of ice in particular in regrowth thereby e.g. minimising potential freezing damage e.g. by preventing or inhibiting ice recrystallisation of the product upon freezing, said process comprising addition of a host organism capable of expression of a foodgrade recombinant polypeptide or protein with an amino acid sequence substantially corresponding to that of AFP type III HPLC 12 to the non improved product as such or to an ingredient or mixture normally used to prepare the non improved product and subsequently subjecting the host organism to conditions such that the nucleic acid sequence encoding AFP type III HPLC 12 is expressed in the product or ingredient or mixture by carrying out a polypeptide production process according to the invention as disclosed elsewhere in the description in addition to the steps normally taken to prepare the non improved product also falls within the scope of the invention. The product can suitably be a food product or a biological material. The biological material can for example be an animal organ or tissue or be plant material. In particular recombinant polypeptide can be added. Preferably the polypeptide will be of foodgrade status in order to provide the final product with food grade status. A process wherein the product to be improved is a food product is preferred. A specific embodiment of a suitable polypeptide for a process according to the invention is a yeast AFP as illustrated in the Examples. The host organism can either be destroyed or damaged during or after the production process in order to release the AFP polypeptide or protein into the mixture or ingredient of the product or into the product per se. Such destruction or damage can occur in a number of manners known to a person skilled in the art, whereby care must be taken not to carry out the process under too harsh conditions to prevent loss of AFP activity of the polypeptide or protein. Alternatively a host organism capable of secreting the AFP polypeptide or protein in the ingredient or mixture or food product as such can be used in the production process. For example a baker's yeast can be the host organism in a process for producing a food product such as a bakery product. The production process can be carried out as usual with the only difference being addition of a different yeast i.e. a yeast comprising a DNA construct enabling expression and secretion of a polypeptide or protein substantially corresponding to type-III AFP HPLC-12 in the dough prior to or during baking thus enabling production of dough or baked product with improved freezing properties. Analogously processes wherein bacteria such as lactic acid bacteria are used form suitable embodiments of the invention. Cheese making and yoghurt making processes or other food producing processes requiring fermentation fall within the type of processes covered by the invention.

Advantageously a production process for improving products according to the invention will be carried out without requiring addition of proteases or chemicals after the recombinant polypeptide or protein with amino acid sequence corresponding substantially to AFP-type III HPLC 12 has been expressed or secreted to obtain the AFP polypeptide or protein as monomeric product.

Use of a polypeptide or protein with amino acid sequence corresponding substantially to AFP-type III HPLC 12 in any of the embodiments disclosed above as additive in a product for improvement of said product, said improvement residing in improved properties of modification of ice crystal growth processes influencing size and shape characteristics of ice in particular in regrowth thereby e.g. minimising potential freezing damage e.g. by preventing or inhibiting ice recrystallisation of the product upon freezing, said use occurring in a manner known per se for AFP's to obtain higher specific antifreeze activity than obtainable with Winter Flounder AFP falls within the scope of the invention. Preferably the product will be a food product. The product may suitably be a biological material. The protein or polypeptide may be a recombinant protein or polypeptide.

A preferred embodiment of the process or use for improving products is a process or use, wherein the product is a product destined to be frozen. For food products ice cream is a suitable example. As indicated above a dough or bakery product are also of interest.

Food products comprising food grade recombinant polypeptide or protein with amino acid sequence corresponding substantially to AFP-type III HPLC 12 in any of the embodiments disclosed above as additive in a food product for improvement of said product, said improvement residing in improved properties of modification of ice crystal growth processes influencing size and shape characteristics of ice in particular in regrowth thereby e.g. minimising potential freezing damage e.g. by preventing or inhibiting ice recrystallisation of the product upon freezing fall within the scope of the invention. Such a food product does not comprise naturally occurring edible organisms like Ocean Pout merely comprising sequences encoding a polypeptide or protein having an amino acid sequence corresponding to the amino acid sequence of Ocean Pout HPLC-12 in the form and number in which they occur in nature in the Ocean Pout. A suitable category of products according to the invention is non animal products. Another suitable category is the category of man made products. Plant products are also suitable examples of products according to the invention. Food products according to the invention can be obtained through a process or use for improving a product in any of the embodiments described above.

In particular a food product comprising a food grade recombinant host organism having improved freeze tolerance, said improvement residing in improved properties of modification of ice crystal growth processes influencing size and shape characteristics of ice in particular in regrowth thereby e.g. minimising potential freezing damage e.g. by preventing or inhibiting ice recrystallisation of the product upon freezing, said food grade host organism containing and/or being surrounded by a food grade recombinant polypeptide or protein with an amino acid sequence corresponding substantially to AFP-type III HPLC 12 in any of the embodiments disclosed above and/or capable of expressing and/or secreting such a polypeptide or protein prior to freezing is also claimed.

Such a recombinant food grade host organism furthermore also falls within the scope of protection of the invention. As does a food grade recombinant host organism capable of expressing at least an AFP-encoding nucleic acid sequence, said nucleic acid sequence being comprised in a DNA construct, said DNA construct not being present in the native host organism and said DNA construct comprising in the order given (a) a strong, optionally inducible, promoter active in the host organism, (b) an ATG start codon, that may be present in an optional DNA signal sequence capable of secreting the protein produced by the host organism during expression of the AFP-encoding nucleic acid sequence of (c) below, which signal sequence can be homologous or heterologous to the AFP-encoding nucleic acid sequence and is in reading frame with the ATG start codon, (c) at least one nucleic acid sequence encoding an amino acid sequence substantially corresponding to that of AFP type III-protein HPLC 12, said nucleic acid sequence in reading frame with the ATG start codon, and optionally (d) a stop codon bound to the 3' end of the AFP-encoding nucleic acid sequence.

Suitable embodiments of such a recombinant host organism are described below in the process for polypeptide production and these organisms as such are claimed.

The subject invention is further directed at a process for producing recombinant polypeptides or proteins exhibiting ice crystal growth and form modifying activity, so-called recombinant anti-freeze peptides (AFP) exhibiting a specific anti freeze activity higher than that of Winter Flounder AFP, by 1) cultivating a food grade host organism under conditions whereby expression of at least an AFP-encoding nucleic acid sequence occurs or is induced, said nucleic acid sequence being comprised in a DNA construct, said DNA construct not being present in the native host organism and said DNA construct comprising in the order given (a) a strong, optionally inducible, promoter active in the host organism, (b) an ATG start codon, that may be present in an optional DNA signal sequence capable of secreting the protein produced by the host organism during expression of the AFP-encoding nucleic acid sequence of (c) below, which signal sequence can be homologous or heterologous to the AFP-encoding nucleic acid sequence and is in reading frame with the ATG start codon, (c) at least one nucleic acid sequence encoding an amino acid sequence substantially corresponding to that of AFP type III-protein HPLC 12, said nucleic acid sequence in reading frame with the ATG start codon, and optionally (d) a stop codon bound to the 3' end of the AFP-encoding nucleic acid sequence.

The process can optionally further comprise collecting the product expressed from the AFP-encoding nucleic acid sequence obtained therefrom by further processing in a manner known per se. In order to obtain secretion of the expression product of the nucleic acid sequence encoding an amino acid sequence substantially corresponding to that of AFP type III-protein HPLC 12 the DNA construct can further comprise a signal sequence for the host organism enabling secretion by the host during cultivation of the host. The host organism is suitably a microorganism. Suitable foodgrade microorganisms are fungi such as yeast and bacteria such as lactic acid bacteria. The yeast cells *Saccharomyces cerevisiae, Saccharomyces fragilis Saccharomyces lactis* are examples of a suitable yeast host cell. A person skilled in the art of fermentation processes in food production will know which yeast cells are suitable and which transformation and expression systems are available (Romanos et al, Campbell and Duffus). The lactic acid bacteria *Lactobacillus, Streptococcus* and *Bifidobacterium* are also examples of suitable bacterial host organisms of which many strains are known and for which suitable transformation and expression systems exist as any person skilled in the recombinant DNA work of bacteria associated with dairy produce knows (Gasson, 1993). The FDA has a list of food grade organisms which is available to the public. A person skilled in the art is aware of the organisms that are considered foodgrade i.e. have GRAS (generally recognised as safe) status. In particular organisms associated with fermentation of food products and production of dairy produce are suitable.

The phrase "one nucleic acid sequence encoding an amino acid sequence substantially corresponding to that of AFP type III-protein HPLC 12" comprises any nucleic acid encoding exactly the amino acid sequence of native HPLC-12 from Ocean Pout. Such nucleic acid sequence may differ due to the degeneracy of the genetic code i.e. the fact that different nucleic acid codons encode the same amino acid. In addition a nucleic acid sequence encoding an amino acid sequence that differs by one or two amino acids from the known amino acid sequence but still encodes a polypeptide with the same AFP activity as the native protein is also included within the scope of the invention. The mutations or differences may not be in amino acids known to be essential for activity of the polypeptide. Proline residues are preferably therefore not deleted or replaced. Preferably any differences in amino acid sequence are silent mutations, whereby the substitutions are conservative substitutions that do not alter the hydropathy profile of the polypeptide and thus presumably do not severely influence the polypeptide structure and the activity, i.e. an amino acid with a hydrophobic side chain is preferably only exchanged for another amino acid with a hydrophobic side chain and an amino acid with a hydrophillic side chain is only replaced by another amino acid with a hydrophillic side chain. The amino acid homology between HPLC-12 and HPLC-1 is less than 60%. An amino acid sequence exhibiting homology above 60% preferably more than 70% and most preferably more than 80% can be expected to be representative of a polypeptide exhibiting similar properties to HPLC-12 and thus be considered substantially corresponding to HPLC-12. The phrase "substantially corresponding to" thus includes nucleic acid sequences encoding amino acid sequences that exhibit more than 60% homology to the amino acid sequence of native HPLC-12. In addition the polypeptide encoded by the amino acid sequence should exhibit at least the AFP activity of AFP-type I from Winter Flounder and preferably at least the AFP activity of native HPLC-12. The AFP activity can be determined by carrying out comparisons with recrystallisation assays using a series of dilutions of the polypeptide to be determined and AFP-type I and/or native HPLC-12 as obtained from Ocean Pout blood in the same dilutions as the polypeptide to be tested i.e. comparison of the same w/v of polypeptide or protein. The manner in which such a recrystallisation assay can be carried out and evaluated is illustrated in the Examples. A polypeptide exhibiting any or a number of the above mentioned characteristics may be considered corresponding substantially to HPLC-12.

In a preferred embodiment of the invention the DNA construct and the cultivation conditions of the host organism are such that it secretes a monomeric polypeptide with an amino acid sequence substantially corresponding to that of AFP type III-protein HPLC 12. The DNA construct will thus preferably not express in tandem a dimer or multimer of an amino acid sequence substantially corresponding to that of AFP type III-protein HPLC 12. The production of dimers or multimers will require additional downstream processing steps or can prohibit secretion of an active polypeptide. Preferably the DNA construct will therefore comprise a nucleic acid sequence encoding an amino acid sequence substantially corresponding to that of AFP type III-protein HPLC 12 in the monomeric form. Naturally the DNA construct may comprise multiple copies of the nucleic acid sequence encoding an amino acid sequence substantially corresponding to that of AFP type III-protein HPLC 12 in the monomeric form in tandem.

A further preferred embodiment of the invention involves a DNA construct in which the nucleic acid sequence encoding the amino acid sequence substantially corresponding to AFP-type III HPLC 12 comprises the preferred codons of the host organism of the process. This is preferred in view of the fact that translation efficiency is increased by avoiding certain codons in particular host organisms. Preferred codon usages differ in prokaryotes, in yeast and plants from codon usage found in Winter Flounder. For example the codons GCA, GCG and GCT together account for more than 65% of the alanine codons of known genes of E. coli, S. Cerevisiae and Z. mays, whereas they account for less than 25% of the alanine codons of a fish such as the Winter Flounder. Similarly this is the case for threonine codons ACA, ACG and ACT (PCT/US90/02626). The codon usage as preferred by lactic acid bacteria and yeast can be derived from literature specific for these groups of microorganisms. A person skilled in the art of recombinant DNA technology with these particular expression organisms will know which codons are preferred.

When the host organism is a yeast a preferred embodiment of the DNA construct will comprise the DNA pre-sequence of the α-mating factor of S. cerevisiae as signal sequence. It may also in a further embodiment comprise the pro-sequence of the α-mating factor of S. cerevisiae between the pre-sequence and the AFP-encoding nucleic acid sequence, whereby the pre-sequence, the pro-sequence and the AFP-encoding nucleic acid sequence are in the same reading frame. Alternatively when the host organism is a yeast a preferred embodiment of the DNA construct will comprise the invertase signal sequence of S. cerevisiae preceding the nucleic acid sequence encoding AFP.

When the host organism is a yeast a preferred embodiment of the DNA construct will comprise the inducible GAL7 promoter or a constitutive GAPDH promoter of Saccharomyces cerevisiae. For other host organisms suitable promoters for inclusion in the DNA construct are well known.

The following references are cited as providing examples of possible transformation systems or elements thereof: for yeast Campbell and Duffus, for plants PCT/US90/0626 and van den Elzen et al (1985) and for animals Hanahan, (1988).

Prior to the subject invention no substantially isolated and purified foodgrade recombinant polypeptide or protein substantially equivalent to type-III AFP HPLC-12 exhibiting such high AFP activity had been produced. For the first time substantially isolated foodgrade recombinant polypeptide or protein substantially equivalent to type-III AFP HPLC-12 exhibiting AFP activity higher than that of Winter Flounder has been produced. The invention covers substantially pure and isolated recombinant foodgrade polypeptide or protein exhibiting improved properties of modification of ice crystal growth processes influencing size and shape characteristics of ice in particular in regrowth thereby e.g. minimising potential freezing damage e.g. by preventing or inhibiting ice recrystallisation upon freezing, so-called recombinant anti-freeze peptides (AFP) exhibiting AFP activity higher than of an equal amount of Winter Flounder AFP-type-I, said polypeptide or protein having an amino acid sequence substantially corresponding to that of AFP type III-protein HPLC 12. Such recombinant polypeptides and in particular recombinant polypeptides or proteins exhibiting the above modified activity such as ice crystal growth inhibiting activity, so-called recombinant anti-freeze peptides (AFP) exhibiting a specific anti freeze activity higher than that of Winter Flounder AFP, prepared by a process according to any of the preceding embodiments of the invention also fall within the scope of the invention.

2. Materials and Methods 2.1. Strains and Growth Conditions.

E. coli strain JM109 (endA1, recA1, syrA96, thi, hsdR17, rk⁻, mk⁺ relA1 supE44, Yanisch-Perron, et al, 1985) was used for amplification of plasmids. S. cerevisiae strain SU50 (MATa, cir°, leu2, his4, can1; Verbakel, 1991) was used for transformation of the multicopy integration plasmids. E. coli transformants were selected for on Luria agar plates containing 100 μg ampicillin ml⁻¹ Sambrook et al (1989). Yeast strains were maintained on selective YNB-plates (0.67% Difco Yeast Nitrogen Base without amino acids, 2% glucose, 2% agar) supplemented with the essential amino acids (histidine 20 μg/ml, uracil 20 μg/ml). The same liquid medium was used for pre-cultures, which were grown for 48 hours at 30° C. and diluted 1:10 in YP medium (1% Difco yeast extract, 2% difco peptone) containing 5% galactose fox induction of the GAL7 promoter.

Plasmids

The relevant details of the AFP-III containing plasmids are given in table 1.

Transformation

Transformation of JM109 was according to Chung et al., (1989). Transformation of the yeast strains was performed by electroporation, mainly as described by Becker et al (1991). Transformants were recovered on selective YNB-plates. A person skilled in the art will realise that various transformation methods are possible. Alternatives depend on the organism to be transformed and are well documented in various handbooks such as Sambrook et al (1989) and Campbell and Duffus (1988).

Molecular Biological Procedures

Restriction enzymes and DNA modification enzymes were applied as recommended by the supplier.

Oligonucleotides were synthesized on an Applied Biosystems 380A DNA synthesizer and purified by standard procedures.

Purification of AFP-III

The AFP III from Ocean Pout, *Macrozoarces americanus*, was purified from the blood of fish caught in the coastal seawaters of Newfoundland. The AFP III sample was prepared by centrifugation of the clotted fish serum as described by Hew et al, (1984).

Cation Exchange Chromatography.

Cation exchange chromatography was performed on a Mono S column (HR5/5, Pharmacia Biotech) on the SMART system (Pharmacia Biotech). Sample buffer was 10 mM $Na_2HPO_4/NaH_2PO_4$ (Merck) pH 6.0 and the elution was done with a 0-0.5 M NaCl (Merck) linear gradient, with a flow of 100 μl/min. Peptides were detected using the μ Peak Monitor (Pharmacia Biotech) at 214 and 280 nm. Fractions were collected monitoring the 214 nm signal using the integrated SMART system fraction collector, system temperature was set at 15° C.

Reversed Phase High Performance Liquid Chromatography.

Reversed phase high performance liquid chromatography (RP-HPLC) was performed using a μRPC C4/C18 SC2.1/10 column (Pharmacia Biotech) on the SMART system (Pharmacia Biotech). The sample was applied to the column in 0.06% Trifluoroacetic acid (TFA, Merck) in Milli Q water (Solvent A) and eluted using 80% Acetonitrile (Merck), 0.054% TFA in Milli Q water (Solvent B). The used standard gradient was programmed as follows: 0 min. 100% solvent A, 5 min. 100% solvent A, 10 min. 65' solvent A, 50 min. 40% solvent A, 55 min. 0% solvent A, 57.5 min. 0% solvent A and at 58 min. 100% solvent A at a flow of 100 μl/min. Peptides were detected with the μPeak Monitor (Pharmacia Biotech) at three wavelenghts 214, 256 and 280 nm. Peaks were collected monitoring the 214 nm signal using the integrated SMART system fraction collector, system temperature was set at 20° C.

AFP-III isoforms 1, 2 and 3 were separated by means of a modified gradient: 0 min 100% solvent A, 10 min 60% solvent A, 35 min 55% solvent A, 36 min 45% solvent A, 45 min 45% solvent A, 46 min 0% solvent A, 50 min 0% solvent A, 50.1 min 100% solvent A and 60 min 100% solvent A. Buffers and all SMART system details are the same as those used with the standard gradient.

Sodium-dodecyl-sulphate polyacrylamide gel electrophoresis.

16% polyacrylamide Tricine gels (Novex) were run on an Xcell electrophoresis cell (Novex) according to the suppliers protocol. Sample buffer was from Novex and consisted of 3.0 ml TRIS-HCl 3.0 M, 2.4 ml Glycerol, 0.8 g SDS, 1.5 ml 0.1% Coomassie Blue G, 0.5 ml 0.1% Phenol Red and 5% β-mercaptoethanol, final volume was adjusted to 10 ml with distilled water, pH=8.45). Running buffer was also from Novex and contained 12.1 grammes TRIS, 17.9 grammes Tricine and 1 gram SDS in a total volume of 1 litre of distilled water, the pH value was approximately pH 8.3. The gel was coloured using 10% Coomassie Brilliant Blue R250 (Bio-Rad) dissolved in a solution of 40% Ethanol (Merck), 10% Acetic Acid (Merck) and 50% distilled water, this solution was heated in a microwave for 45 seconds, then the gels were stained for 15 minutes on a rotary shaker. Gels were destained with a solution of 10% Ethanol (Merck), 7.5% Acetic Acid (Merck) and 82.5% distilled water. In case of molecular weight determination MARK 12 prestained markers (Novex) were used.

Western Blotting.

Novex Tricine gels were blotted using trans-blot transfer medium (Bio-Rad) on the western transfer blot module (Novex) according to the supplier protocol. After blotting the membrane was blocked with 5% skimmed milk in 150 mM NaCl, 50 mM Tris/HCl pH 7.4 and afterwards incubated in 1% skimmed milk in 150 mM NaCl, 50 mM Tris/HCl, 0.1% Tween 20, pH 7.4 and a monoclonal antiserum against Ocean Punt antifreeze peptides. Two different antibodies were obtained (gifts from M. M Gani, Unilever Research, Colworth House Laboratory), one for the determination of the S groups and the other one for the determination of the Q group. Incubation was performed overnight at room temperature under soft agitation. Unabsorbed antibodies were removed by washing with the incubation buffer (3×5 min) The membrane was incubated with the second antibody (Goat anti-mouse IgG (H+L), Alkaline Phosphatase Conjugate; BioRad, Richmond) for 2 hours at room temperature. The enzyme was developed using BCIP/NBT (Biorad).

Tryptic Digestion.

For trypsin digestion, the sample dissolved in 0.1 M $NH_4HCO_3$ buffer pH 8.3. Trypsin (TPCK treated, Worthington, Millipore Corporation) was added in an enzyme:substrate ratio of 1:100. After 30 minutes the pH was checked and the same amount of trypsin was added once more. Incubation was carried out overnight at 37° C. The digestion was stopped by the addition of TFA to yield a pH value of pH 2. Peptides were separated by means of RP-HPLC on the SMART system (Pharmacia).

N-Terminal Amino Acid Sequence Analysis.

N-terminal amino acid sequence analysis was performed on a LF 3000 Protein Sequencer (Beckman) according to the suppliers protocol. The PTH-derivatives of the amino acids were analyzed on an automated RP-HPLC system, system Gold (Beckman).

Protein Determination by Amino Acid Analyses.

The AFP-III samples were hydrolysed in 6 M HCl containing 1% Phenol under vacuum at 110° C. for 24 hours and then dried. Analyses were performed on an Alpha plus series 2 amino acid analyzer (Pharmacia Biotech) using the suppliers protocol.

Recrystallisation Assay

Samples to be tested for AFP-III activity were mixed with sucrose powder to give a 30% by volume sucrose solution. A proportion of this solution was placed on a microscope slide, covered with a cover slip to prevent evaporation and set on a Linkam THMS cold stage, connected with a Linkam CS 196 cooling system and controlled by a Linkam TMS 91 controller. This solution was crash cooled to −40° C. (δ 99° C./min.) and subsequently heated to −6° C. The growth of ice crystals was examined microscopically over the course of 30 minutes incubation at −6° C.

For assay of HPLC purified peptides, samples from the RP-HPLC column containing purified AFP-III isoforms were dried in a Speed Vac Concentrator (Savant) twice after one rehydration step in Milli Q water. After the second drying step the samples were solubilized in 100 μl of Milli Q water and the pH was checked to make sure that all of the TFA from the RP-HPLC buffer system had been removed. Samples were diluted to an absorbance value of 0.700 at λ=214 nm, this is equivalent to an approximately 0.1 μg/ml fish AFP-III solution. To make sure that the samples contained an equal amount of AFP-III, they were later checked by amino acid analysis. When purified samples, AFP-III isoforms, were used, their purity was checked by N-terminal amino acid sequence analysis.

Fed Batch Fermentation.

Inoculation procedure: a culture of the appropriate transformant was grown 25 ml minimal medium and cultured overnight at 30° C. and 300 rpm. The culture was subsequently transferred to a 1000 ml shake flask containing 500 ml YP containing 2% glucose and cultured overnight at 30° C. and 300 rpm. This culture was used as inoculum for the fed batch experiment.

The following batch medium was used: 110 g glucose.1H$_2$O made up to 500 g with demineralised water. 25 g Trusoy, 50 g yeast-extract (Ohly), 10.5 g K$_2$HPO$_4$, 5 ml 1000× Egli vitamin solution, 50 ml 100× Egli tracer metals (Egli, 1980), 0.25 g L-Histidine.HCl (Sigma), 3 g MgSO$_4$., 2 g antifoam to 4500 g with demineralised water. The glucose solution was heat-sterilised and the vitamin solution was filter-sterilised separately. All other components were heat sterilised in the fermenter. The temperature was regulated at 30° C. and the pH to a value of 5.0. The fermenter was inoculated and the cells were cultured at an air flow of 2 l/min and a stirrer speed of 600 rpm. After 18 hours the feed phase was started.

The following feed medium was used: 1100 g glucose.1H$_2$O made up to 1750 g with demineralised water. 62.5 g yeast-extract (Ohly), 30 g K$_2$HPO$_4$, 5 ml 1000× Egli vitamin solution, 50 ml 100× Egli tracer metals (Egli, 1980), 6.25 g L-Histidine.HCl (Sigma), 6.25 g MgSO$_4$.7H$_2$O, 2 g antifoam to 850 g with demineralised water.

The feed pump was regulated to a constant RQ-value (ratio of moles CO$_2$ produced and moles O$_2$ consumed) of 1.05, based on software tools as described by Keulers (1993). The culture was harvested after 37 hours.

EXAMPLE 1

Construction of a Synthetic Gene Encoding a Type III AFP

A nucleotide sequence encoding the HPLC I antifreeze peptide, optimised for expression in *Saccharomyces cerevisiae* was constructed as follows: a set of 12 oligonucleotides was synthesized (invafp1, invafp2, invafp3, invafp4, invafp5 invafp6, invafp7, invafp8, invafp9, invafp10, invafp11 and invafp12), mainly comprising the DNA sequence of the mature AFP expressed in preferentially used *S. cerevisiae* codons. The synthetic gene was designed to contain 5′ single stranded regions compatible with PstI and HindIII generated sticky ends. (FIG. 2)

For the assembly of the synthetic AFP gene, 50 pmol of each of the oligonucleotides were dissolved in 12 μl water, incubated for 2 min. at 95° C., and directly placed on ice. After this denaturation step, the oligonucleotides were phosphorylated in a final volume of 20 μl, containing 2.5 mM ATP, 5 mM DTT and about 10 U of polynucleotide kinase, for 40 min. at 37° C., followed by a 2 min denaturation at 95° C. and placement on ice. 10 μl of each phosphorylated oligonucleotide was mixed with their most complementary DNA oligonucleotide to obtain duplex formation. After 2 min incubation at 95° C. for denaturation, each duplex was cooled slowly to 30° C. Again 101 of all six duplex mixtures were pooled and incubated in a final volume of 100 μl, containing 50 mM Tris/HCl, pH 7.5, 8 mM MgCl$_2$, 8 mM DTT, and 40 μg/ml gelatine and 10 U of DNA ligase, for two hours at 20° C. The ligation mix was then precipitated, and redissolved in 30 μl of TE-buffer. 15 μl of the mixture were placed on a 2% agarose gel, and the DNA band of the expected size (approximately 224 base pairs) was cut out of the gel and finally purified through the Gene Clean II procedure, as recommended by the supplier.

The obtained DNA fragment was then ligated into the PstI/HindIII linearized vector pTZ19R (Pharmacia) and transformed into *E. coli* JM 109 by standard procedures. Plasmid DNA of several transformants was isolated by the slightly modified alkaline-lysis mini-preparation method and analyzed by restriction analysis with several enzymes. The sequence of the insert contained in one such plasmid was confirmed by Sanger dideoxy sequencing of the double stranded plasmid (Sanger et al, 1977). This intermediate construct, containing the coding region of the synthetic AFP-III cassette was named pUR7700 (FIG. 3).

EXAMPLE 2

Construction of Yeast Expression Vectors Containing a Synthetic Gene Encoding AFP-III HPLC-1

The synthetic AFP-III gene carried by pUR7700 contains none of the information required for expression of this peptide in yeast. To obtain expression and secretion of this gene, constructs containing translational fusions of the AFP-III gene with a suitable secretion signal sequence must be made and these fusion sequences brought under the control of a yeast gene promoter.

Suitable secretion signal sequences can be selected from a variety of genes encoding proteins efficiently secreted by yeast. eg invertase encoded by SUC2 or α mating factor, encoded by MFα1 and MFα2. To obtain a suitable fusion with the invertase signal sequence, a PCR fragment was generated containing the invertase signal sequence, part of the GAL7 promoter and a suitable restriction enzyme site to ensure in frame fusion of the invertase signal sequence with the synthetic AFP-III gene.

To obtain this fragment a PCR primer, invafp14, was designed with the following sequence:

```
                                              (SEQ ID NO: 4)
                                   NheI    BamHI
3' CCA AAA CGT CGG TTT TAT AGA CGATCG CCTAGGGC 5'
invafp14
```

This primer was used as the 3′ primer in a PCR reaction in combination with the 5′ primer PG7 05 AF (Verbakel, 1991) which hybridizes with the sequence found in the GAL7 promoter. Using pUR2778 plasmid DNA as template (FIG. 4, van Gorcom et al, 1991) the reaction generated an approximately 243 bp fragment. This fragment was eluted from an agarose gel and purified by the Gene Clean procedure according to the manufacturers instructions. The purified fragment was subsequently digested with SacI and BamHI and the resulting approximately 88 bp fragment ligated into the appropriate sites in plasmid pTZ19R. The ligation mix was introduced into E. coli JM109 by transformation and plasmid DNA isolated from one transformant and sequenced to confirm the identity of the cloned insert. This plasmid was designated pUR7701 (FIG. 5).

To obtain an in frame fusion of the invertase signal sequence with the synthetic AFP-III gene pUR7700 was digested with NheI and HindIII and the approximately 196 bp fragment isolated and ligated with the approximately 2911 bp fragment formed by digestion of pUR7701 with NheI and HindIII. The resulting plasmid was named pUR7702 (FIG. 6).

In a similar manner, a PCR fragment containing the α mating factor pre-pro signal sequence was generated using primer MFαAFPIII as 3' primer:

```
                                          (SEQ ID NO: 5)
                          NheI
3' CTA TTT TCT CTC CGA CTT CGATCGCC 5' MFαAFPIII
```

A PCR fragment containing part of the GAL7 promoter and all of the pre-pro a mating factor coding sequence was generated from a pUR2660 (WO 94/03617) DNA template using MFαAFPIII and PG7 05 AF as primers. pUR2660 contains the pre-pro α mating factor sequence under the control of the GAL7 promoter. The resulting approximately 462 bp fragment was purified as described above and digested with SacI and NheI. The approximately 292 bp fragment so obtained was ligated into the approximately 3025 bp fragment obtained by digestion of pUR7702 with SacI and NheI. Plasmid DNA from several E. coli JM109 transformants obtained from this ligation was sequenced to confirm that the correct fragment had been cloned. One of these plasmids was designated pUR7703 (FIG. 7).

To construct plasmids capable of expressing the AFP-III cassette in yeast the synthetic gene-signal sequence fusions were introduced into a variety of yeast expression vectors as follows:

The approximately 278 bp SacI/HindIII fragment of pUR7702 and the approximately 488 bp SacI/HindIII fragment of pUR7703, which carry the invertase and a mating factor fusions to AFP-III respectively, were cloned independently using standard techniques into yeast expression vectors also digested with SacI and HindIII. These expression vectors both carry the S. cerevisiae GAL7 promoter such that insertion of genes at the SacI site enables GAL7 directed transcription of the inserted genes.

pUR7704 (FIG. 8) was made by insertion of the invertase signal sequence AFP-III cassette from pUR7702 into the multi-copy ribosomal DNA integration vector pUR2778 and pUR7706 (FIG. 9) is pUR2778 containing the a mating factor AFP-III cassette, derived from pUR7703, inserted between the SacI and HindIII sites.

EXAMPLE 3

Expression of AFP-III in S. cerevisiae

Plasmids pUR7704 and pUR7706 were linearized by digestion with HpaI which targets integration of the plasmids to the yeast rDNA region then subsequently independently introduced into S. cerevisiae strain SU50 by electroporation. Transformants were selected through their ability to grow in the absence of leucine. To achieve expression of the cloned AFP-III genes, transformants carrying pUR7704 or pUR7706, were first grown for 40 hours in liquid minimal medium at 30° C. then subsequently diluted 1:10 in freshly prepared induction medium (Yeast extract 1%, Difco peptone 2%, galactose 5%) and incubated at 30° C. for a further 48 hours. At the end of this period samples of the culture supernatant were tested for their ability to inhibit the growth of ice crystals.

The growth of ice crystals was examined microscopically over the course of 30-minutes incubation at −6° C. It was clearly demonstrable that supernatant samples derived from yeasts carrying the synthetic AFP-III gene had an inhibitory effect on ice crystal growth when compared to similar, control, samples prepared from the supernatants of untransformed yeasts or yeasts carrying the expression vector but lacking the synthetic AFP-III gene. However, the recrystallisation inhibition activity of the yeast produced material was significantly less than that of an equivalent amount of fish AFP preparation.

For further analysis of the produced antifreeze peptide, 10 ml samples form the induced culture of pUR7704 and pUR7706 transformants were centrifuged for 5 min at 4000 rpm and the cells and supernatants collected and stored at −20° C. Denaturating SDS polyacrylamide gel electrophoresis was used to separate the proteins and the AFP was detected by western blotting using an anti-AFP specific monoclonal antibody.

The presence of a band with an apparent molecular weight of 6.5 kD in the supernatant samples from the yeast transformant carrying pUR7704 and pUR7706 clearly shows that these transformants are capable of the production of AFP-III. The peptide was purified by reversed phase HPLC and the N terminal sequence was determined. This sequence demonstrated that the HPLC-1 peptide was correctly processed and secreted by the yeast.

EXAMPLE 4

Identification of the Most Active Ocean Pout Antifreeze Peptide Subtype

Isoforms from AFP-III were purified using a two step procedure. First the sample was loaded onto a cation exchange mono S column and eluted using the described gradient. The elution pattern is shown in FIG. 10. One non retarded peak (the Q peak) and four eluted peaks (S1 to S4) were isolated from the column. S1 represents the protein with the lowest binding capacity to the Mono S cation exchange column under these conditions and S4 contains the protein with the highest binding capacity to the column. The peaks were collected and loaded onto a RP-HPLC column using the described gradient. The chromatogram from the total material is shown in FIG. 11. The peaks are the AFP-III isoforms and are numbered from 1 to 12 according to their behaviour on this column using the specified conditions. All AFP-III isoforms elute between 25 and 45 minutes. The RP-HPLC chromatograms of the Q and S1 to S4 fractions are shown in FIG. 12 to 16. Fractions each yield different AFP-III isoforms and which AFP isoform was contained in each peak is summarized in table 2. Fractions collected from the Mono S and RP-HPLC columns were tested with mouse anti-AFP-III antiserum and all isoforms from S1 to S4 gave a positive reaction to the S type antiserum, isoform 12 from the Q group reacted positively to the Q type antiserum. The N-terminal amino acid sequence was determined from five of the isoforms (Table 3). The AFP-III HPLC 7 peak was contaminated with fish lysozyme but the other amino acid sequences identified could be related to the known sequences of the AFP-III isoforms. Equal amounts of the purified proteins, were tested for antifreeze activity.

As evidenced by recrystallisation inhibition assay only the HPLC-12 isoform of AFP-III showed significant antifreeze activity. To confirm this finding the Ocean Pout AFP-III isoforms were reconstituted in the presence and absence of the HPLC-12 isoform. The completely reconstituted peptide preparation maintained the activity of the crude fish preparation whereas the preparation lacking the HPLC-12 isoform showed greatly reduced antifreeze activity as evidenced by the recrystallisation assay.

Using a tryptic digest of isoform 12 the total amino acid sequence of this isoform was determined. The sequence was found to be identical to that described in the literature (Davies and Chow, 1990).

EXAMPLE 5

Construction of a Synthetic Gene Encoding the HPLC-12 Variant of Type III AFP.

A nucleotide sequence encoding the HPLC-12 antifreeze peptide, linked to the invertase signal sequence and with codon usage optimised for expression in *Saccharomyces cerevisiae*, was constructed as follows: a set of 15 oligonucleotides was synthesized (HPLC12.1, HPLC12.2, HPLC12.3, HPLC12.4, HPLC12.5, HPLC12.6, HPLC12.7, HPLC12.7, HPLC12.8, HPLC12.9, HPLC12.10, HPLC12.11, HPLC12.12, HPLC12.13, HPLC12.14 and HPLC12.15), mainly comprising the DNA sequence of the mature AFP expressed in preferentially used *S. cerevisiae* codons. The synthetic gene was designed to contain single stranded regions compatible with SacI and HindIII generated sticky ends. (FIG. 17)

For the assembly of the synthetic HPLC-12 gene, 50 pmol of each of the oligonucleotides were dissolved in 12 µl water, incubated for 2 min. at 95° C., and directly placed on ice. After this denaturation step, the oligonucleotides were phosphorylated in a final volume of 20 µl, containing 2.5 mM ATP, 5 mM DTT and about 10 U of polynucleotide kinase, for 40 min. at 37° C., followed by a 2 min denaturation at 95° C. and placement on ice. 10 µl of each phosphorylated oligonucleotide was mixed with their most complementary DNA oligonucleotide to obtain duplex formation. After 2 min incubation at 95° C. for denaturation, each duplex was cooled slowly to 30° C. Again, 10 µl of all the duplex mixtures were pooled and incubated in a final volume of 100 µl, containing 50 mM Tris/HCl, pH 7.5, 8 mM MgCl$_2$, 8 mM DTT, and 40 µg/ml gelatine and 10 U of DNA ligase, for two hours at 20° C. The ligation mix was then precipitated, and redissolved in 30 µl of TE-buffer. 15 µl of the mixture were placed on a 2% agarose gel, and the DNA band of the expected size (approximately 291 base pairs) was cut out of the gel and finally purified through the Gene Clean II procedure, as recommended by the supplier.

This fragment was ligated with a vector fragment derived from the multi-copy integration vector pUR2778 by digestion with SacI and HindIII. The sequence of the insert was confirmed and the resulting plasmid was named pUR7718 (FIG. 18).

Plasmid pUR7718 was linearized by digestion with HpaI which targets integration of the plasmid to the yeast rDNA region and was then subsequently introduced into *S. cerevi-siae* strain SU50 by electroporation. The resulting transformants were selected through their ability to grow in the absence of leucine.

To achieve expression of the cloned HPLC-12 gene, transformants carrying pUR7718 were first grown for 40 hours in liquid minimal medium at 30° C. then subsequently diluted 1:10 in freshly prepared induction medium (Yeast extract 1%, Difco peptone 2%, galactose 5%) and incubated at 30° C. for a further 48 hours. At the end of this period samples of the culture supernatant were tested for their ability to inhibit the growth of ice crystals.

The results (recrystallisation assay) clearly show that the culture supernatants had high levels of antifreeze activity. Comparison of these results with those obtained for the yeast expression of the HPLC-1 variant showed that the supernatant from the transformant which produced the lowest level of HPLC-12 antifreeze activity exceeded that from the best HPLC-1 transformant.

A fed batch fermentation was performed with a SU50 transformant carrying pUR7718. At the end of the feed phase, the cells were harvested by centrifugation in a Jouan LR 5.22 centrifuge using 1 l buckets, for 30 min at 4650 rpm (7200 g). The supernatant was tested for antifreeze activity by the ice recrystallisation inhibition test. Undiluted supernatant clearly prevents crystal growth, which demonstrates the presence of high levels of active antifreeze peptide in the culture supernatant.

A western blot of the supernatant from this fermentation showed that AFPIII-HPLC12 material was secreted. The apparent molecular weight of the yeast produced HPLC12 was equivalent to that of the fish produced HPLC12. Purification and amino acid sequencing of the yeast produced peptide confirmed that this material was indistinguishable from the HPLC12 peptide produced by Ocean Pout.

REFERENCES

Campbell, I and Duffus, J. H., (1988) Yeast, a practical approach. IRL press, Oxford.

Chao, H., Davies, P. L., Sykes, B. D. and Sonnichsen, (1993) Use of proline mutants to help solve the NMR solution structure of Type III antifreeze protein. Protein Science 2 1411-1428.

Chao, H., Sonnichsen, F. D., DeLuca, C. I., Sykes, B. D. and Davies, P. L. (1994) Structure-function relationships in the globular type III antifreeze protein: identification of a cluster of surface residues required for binding to ice. Protein Science 3 1760-1769.

Chung, C. T., Niemela, S, L., Miller, R. H., (1989), One-step preparation of competent *E. coli*: Transformation and storage of bacterial cells in the same solution. Proc. Natl. Acad. Sci. USA, 86; 2172-2175.

Davis, P. L. and Chow, H. L., (1990), Biochemistry of fish antifreeze proteins, The FASEB. Journal 4 R2460-2468.

Driedonks, R. A., Toschka, H. Y. van Almkerk, J. W, Schäffers and Verbakel, J. M. A. (1995) Expression and secretion of antifreeze peptides in the yeast *Saccharomyces cerevisiae* Yeast 11.

Egli, T. (1980), Wachstum von methanol assimelerende Hefen, PhD Thesis, Zurich no 6538.

van den Elzen et al. (1985) Plant Mol. Biol., 5: 149-154.

Erhart, E., Hollenberg, C. P., (1981), Curing of *Saccharomyces cerevisiae* 2 µm DNA by transformation. Curr. Genet., 3, 83-89.

Fletcher, G. L. Hew, C. L. Joshi, S. B. and Wu, Y. (1994) Antifreeze polypeptide-expressing microorganisms useful in fermentation and frozen storage of foods. US Patent application.

Gasson, M. J., (1993), progress and potential in the biotechnology of lactic acid bacteria F.E.M.S. microbiology Reviews 12 3-20.

Hanahan, (1988) Ann. Rev. Genetics 22: 479-519.

Hew, C. L. Slaughter, D., Shashikant, B. J., Fletcher G. L. and Ananthanarayanan V. S. (1984) Antifreeze peptides from the Newfoundland Ocean Punt *Macrozoarces americanus*: presence of multiple and compositionally diverse components. J. Comp Physiol B. 155, 81-88.

Hew, C. L., Wang, N—C., Joshi, S., Fletcher, G. L., Scott, G. K., Hayes, P. H., Buettner, B. and Davies, P. L., (1988), Multiple genes provide the basis for antifreeze protein diversity and dosage in Ocean Punt. J. Biol. Chem. 263, 12049-12055.

Keulers, M., (1993) PhD thesis technical university of Eindhoven

Li, X., Trinh, K. Y. and Hew, C. L. (1992), Expression and characterization of an active and thermally more stable recombinant antifreeze polypeptide from Ocean Punt, *Macrozoarces americanus*, in *Escherichia coli*: improved expression by modification of the secondary structure of the mRNA. Protein Engineering 4 995-1002.

McKown, R. L. and Warren G. J. (1991) Enhanced survival of yeast expressing an antifreeze gene analogue after freezing. Cryobiology 28, 474-482.

Romanos, M. A., Scorer, C. A. and Clare, J. J., (1992), Foreign Gene expression in yeast: a review, Yeast 8 423-488.

Sambrook, J., Fritsch, E. F., Maniatis, T., (1989). Molecular cloning. A laboratory manual. Second edition Cold Spring Harbor Laboratory, Cold Spring Harbor, New York.

Sanger, F., Nicklen, S. and Coulson, A. R. (1977), DNA sequencing with chain-terminating inhibitors. Proc. Natl. Acad. Sci. USA 74: 5463-5467.

Sonnichsen, F. D., Sykes, B. D., Chao, H. and Davies, P. L., (1993), The non-helical structure of antifreeze protein type III, Science 259, 1154-1157.

Toschka H. Y., Verbakel, J. M., Almkerk J. W. (1992), PCT-Patent Application WO94/03617 with priority of 29 Jul. 1992 from Dutch patent Application 92202338.7 Process for producing Antifreeze Peptides (AFP's).

Van Gorcom, R. F. M., Hessing, J. G. M., Maat, J. and Verbakel, J. M. A., (1991) Xylanase Production. International Patent WO 91/19782.

Verbakel, J. M. A., (1991), Heterologous gene expression in the yeast *Saccharomyces cerevisiae*. PhD. Thesis, University of Utrecht.

Warren, G. J., Hague, C. M., Corroto, L. V. and Mueller, G. M. (1993) Properties of engineered antifreeze peptides. FEBS Letters 321, 116-120.

Yanisch-Perron, C., Viera, J., Messing, J., (1985), Improved M13 phage cloning vectors and host strains: Nucleotide sequence of the M13 mp18 and pUC19 vectors. Gene 33, 103-119.

FIGURE DESCRIPTION

FIG. 1. Isoforms of type III AFP. The boxed regions represent regions of identity and the shaded amino acids are those identified as important for the antifreeze properties of the peptides (SEQ ID NO: 2 and 17-32).

FIG. 2. Synthetic gene encoding AFP-type III HPLC1 (SEQ ID NO: 1).

FIG. 3. Schematic representation of the construction of pUR7700, a plasmid carrying the synthetic AFP-III gene.

FIG. 4. Restriction map of the yeast expression vector pUR2778.

FIG. 5. Schematic representation of the construction of pUR7701, a plasmid carrying the invertase signal sequence.

FIG. 6. Schematic representation of the construction of pUR7702, a plasmid carrying the synthetic AFP-III gene linked in frame to the invertase signal sequence.

FIG. 7. Schematic representation of the construction of pUR7703, a plasmid carrying the synthetic AFP-III gene fused in frame with the mating factor pre-pro secretion signal sequence.

FIG. 8. Schematic representation of the construction of plasmid pUR7704, a multicopy rDNA integration vector carrying the synthetic AFP-III gene linked in frame to the invertase signal sequence.

FIG. 9. Schematic representation of the construction of plasmid pUR7706, a multicopy rDNA integration vector carrying the synthetic AFP-III gene linked in frame to the pre-pro mating factor signal sequence.

FIG. 10. The elution pattern of Ocean Pout antifreeze peptides from a Mono S column.

FIG. 11. Chromatogram of antifreeze peptides separated by reversed phase HPLC.

FIG. 12. Chromatogram of Mono S S1 antifreeze peptides separated by reversed phase HPLC.

FIG. 13. Chromatogram of Mono S S2 antifreeze peptides separated by reversed phase HPLC.

FIG. 14. Chromatogram of Mono S S3 antifreeze peptides separated by reversed phase HPLC.

FIG. 15. Chromatogram of Mono S S4 antifreeze peptides separated by reversed phase HPLC.

FIG. 16. Chromatogram of Mono S S1 antifreeze peptides separated by reversed phase HPLC.

FIG. 17. Synthetic gene encoding type III AFP HPLC12 invertase signal sequence fusion protein (SEQ ID NO: 14-16).

FIG. 18. Schematic representation of plasmid pUR7718.

TABLE 1

AFP-III containing plasmids

| Plasmid Name | Relevant Characteristics |
| --- | --- |
| pUR7700 | pTZ19 carrying HPLC-1 synthetic gene. |
| pUR7701 | pTZ19 carrying invertase signal sequence. |
| pUR7702 | pTZ19 carrying invertase signal sequence-HPLC-1 fusion gene. |
| pUR7703 | pTZ19 carrying mating factor α signal sequence-HPLC-1 fusion gene. |
| pUR7704 | Yeast expression vector carrying invertase signal sequence-HPLC-1 fusion gene. |
| pUR7706 | Yeast expression vector carrying mating factor α signal sequence-HPLC-1 fusion gene. |
| pUR7718 | Yeast expression vector carrying invertase signal sequence-HPLC-12 fusion gene. |

TABLE 2

Mono S fractions containing AFP-III 3 isoforms.

| Mono S Fraction | AFP 3 isoform |
| --- | --- |
| Q | 12 |
| S1 | 4 |
|  | 5 |
|  | 6 |

TABLE 2-continued

Mono S fractions containing AFP-III 3 isoforms.

| Mono S Fraction | AFP 3 isoform |
|---|---|
| S2 | 1 |
|  | 2 |
|  | 3 |
|  | 11 |
| S3 | 7 |
| S4 | 7 |
|  | 9 |

TABLE 3

N-terminal amino acid sequence of AFP-III isoforms.

Lysozyme of Ocean Pout, the peptide formerly referred to as
AFP 3 isoform 7 (SEQ ID NO: 6)
```
                          10                          20
Lys-Val-Phe-Asp-Arg-?-Glu-Trp-Ala-Arg-Val-Leu-Lys-Ala-Asn-Gly-Met-Asp-Gly-Tyr- 21                        30                          40
Arg-Gly-Ile-Ser-Leu-Ala-Asn-Trp-Val-?-Leu-Ser-Lys-Trp-Glu-Ser-?-Tyr-?-Thr-
```

Isoform number 9 (SEQ ID NO: 7)
```
                          10                          20
Ser-Gln-Ser-Val-Val-Ala-Thr-Tyr-Leu-Ile-Pro-Met-Asn-Thr-Ala-Leu-Thr-Pro-Ala-Met-
```

Isoform number 12 (SEQ ID NO: 8)
```
1                        10
Asn-Cln-Ala-Ser-Val-Val-Ala-Asn-Gln-Leu-Ile-Pro-Ile-Asn-Thr-Ala-Leu-
```

TABLE 4

Amino acid sequence of tryptic peptides of AFP-III isoform number 12.

Peptide no 1:
N-terminus 1-23 (SEQ ID NO: 9)
```
1                        10                                           20
Asn-Gln-Ala-Ser-Val-Val-Ala-Asn-Gln-Leu-Ile-Pro-Ile-Asn-Thr-Ala-Leu-Thr-Leu-Val- 23
Met-Met-Arg
```

Peptide no 2: 24 to 39 (SEQ ID NO: 10)
```
1                                  10
Ser-Glu-Val-Val-Thr-Pro-Val-Gly-Ile-Pro-Ala-Glu-Asp-Ile-Pro-Arg
```

Peptide no 3: 40 to 47 (SEQ ID NO: 11)
Leu-Val-Ser-Met-Gln-Val-Asn-Arg

Peptide no 4: 48 to 61 (SEQ ID NO: 12)
```
1                              10
Ala-Val-Pro-Leu-Gly-Thr-Thr-Leu-Met-Pro-Asp-Met-Val-Lys
```

Peptide no 5: 62 to 66 (SEQ ID NO: 13)
Gly-Tyr-Pro-Pro-Ala

---

The invention claimed is:

1. A method of producing a recombinant polypeptide having an amino acid sequence that shares at least 80% identity with the amino acid sequence of ocean pout antifreeze protein (AFP) type III HPLC 12 (SEQ ID NO: 27) and having an ice recrystallisation inhibition activity greater than that of a Winter flounder type I AFP polypeptide, which method comprises
   (1) providing a yeast comprising a DNA construct that is not present in the native yeast, the DNA construct comprising in the following order:
      (a) a promoter active in the yeast,
      (b) an ATG start codon; and
      (c) at least one nucleic acid sequence encoding said polypeptide, said nucleic acid sequence being in reading frame with the ATG start codon;
   (2) cultivating the yeast under conditions whereby expression of the polypeptide encoded by the nucleic acid sequence occurs or is induced; and optionally
   (3) recovering the recombinant polypeptide expressed from the nucleic acid sequence.

2. The method of claim 1 wherein the DNA construct comprises a signal sequence for the yeast enabling secretion of the recombinant polypeptide by the yeast during cultivation of the yeast.

3. The method of claim 2 wherein the ATG start codon is present in the signal sequence, which signal sequence is heterologous to the nucleic acid sequence encoding the recombinant polypeptide and is in reading frame with the ATG start codon.

4. The method of claim 1 wherein the yeast is *S. cerevisiae*.

5. The method of claim 2 wherein the signal sequence is the pre-sequence of the α-mating factor of *S. cerevisiae* or the invertase signal sequence of *S. cerevisiae*.

6. The method of claim 1 wherein the promoter is an inducible GAL7 promoter or a constitutive GAPDH promoter of *S. cerevisiae*.

7. The method of claim 2 wherein the polypeptide is secreted as a monomer.

8. A method of producing a food product which method comprises producing a recombinant type III HPLC 12 polypeptide by the method of claim 1 and adding the polypeptide to a food product.

9. A method of producing a food product which method comprises performing the method of claim 2 whereby the yeast is present in a food product and secretes the recombinant polypeptide into the food product.

* * * * *

SEQUENCE LISTING

<160> NUMBER OF SEQ ID NOS: 32

<210> SEQ ID NO 1
<211> LENGTH: 215
<212> TYPE: DNA
<213> ORGANISM: Artificial Sequence
<220> FEATURE:
<223> OTHER INFORMATION: clone AFP-III HPLC-1 (coding strand)
<220> FEATURE:
<221> NAME/KEY: CDS

```
<222> LOCATION: (16)..(207)
<220> FEATURE:
<221> NAME/KEY: mat_peptide
<222> LOCATION: (16)..()

<400> SEQUENCE: 1
gccaaaatat ctgct agc caa tct gtt gtt gct act caa ttg att cca atg    51
               Ser Gln Ser Val Val Ala Thr Gln Leu Ile Pro Met
                 1               5                  10 aat act gct ttg act cca gtt atg atg gaa ggt aaa gtt act aat cca    99
Asn Thr Ala Leu Thr Pro Val Met Met Glu Gly Lys Val Thr Asn Pro
         15                  20                  25 att ggt att cca ttt gct gaa atg tct caa att gtt ggt aaa caa gtt   147
Ile Gly Ile Pro Phe Ala Glu Met Ser Gln Ile Val Gly Lys Gln Val
 30                  35                  40 aat act cca gtt gct aaa ggt caa act att atg cca aat atg gtt aaa   195
Asn Thr Pro Val Ala Lys Gly Gln Thr Ile Met Pro Asn Met Val Lys
45              50                  55                  60 aca tat gct gct taagcttg                                          215
Thr Tyr Ala Ala <210> SEQ ID NO 2
<211> LENGTH: 64
<212> TYPE: PRT
<213> ORGANISM: Artificial Sequence
<220> FEATURE:
<223> OTHER INFORMATION: clone AFP-III HPLC-1

<400> SEQUENCE: 2

Ser Gln Ser Val Val Ala Thr Gln Leu Ile Pro Met Asn Thr Ala Leu
 1               5                  10                  15

Thr Pro Val Met Met Glu Gly Lys Val Thr Asn Pro Ile Gly Ile Pro
             20                  25                  30

Phe Ala Glu Met Ser Gln Ile Val Gly Lys Gln Val Asn Thr Pro Val
         35                  40                  45

Ala Lys Gly Gln Thr Ile Met Pro Asn Met Val Lys Thr Tyr Ala Ala
     50                  55                  60

<210> SEQ ID NO 3
<211> LENGTH: 223
<212> TYPE: DNA
<213> ORGANISM: Artificial Sequence
<220> FEATURE:
<223> OTHER INFORMATION: clone AFP-III HPLC-1 (non-coding strand)

<400> SEQUENCE: 3
gatccaagct taagcagcat atgttttaac catatttggc ataatagttt gacctttagc    60
aactggagta ttaacttgtt taccaacaat ttgagacatt tcagcaaatg gaataccaat   120
tggattagta actttacctt ccatcataac tggagtcaaa gcagtattca ttggaatcaa   180
ttgagtagca acaacagatt ggctagcaga tattttggct gca                     223

<210> SEQ ID NO 4
<211> LENGTH: 35
<212> TYPE: DNA
<213> ORGANISM: Artificial Sequence
<220> FEATURE:
<223> OTHER INFORMATION: primer invafp14

<400> SEQUENCE: 4
cgggatccgc tagcagatat tttggctgca aaacc                               35
```

```
<210> SEQ ID NO 5
<211> LENGTH: 26
<212> TYPE: DNA
<213> ORGANISM: Artificial Sequence
<220> FEATURE:
<223> OTHER INFORMATION: primer MFalphaAFPIII

<400> SEQUENCE: 5
ccgctagctt cagcctctct tttatc                                        26

<210> SEQ ID NO 6
<211> LENGTH: 40
<212> TYPE: PRT
<213> ORGANISM: Macrozoarces americanus
<220> FEATURE:
<221> NAME/KEY: UNSURE
<222> LOCATION: (6)..(6)
<223> OTHER INFORMATION: X indicates residue was not unambiguously
      identified
<220> FEATURE:
<221> NAME/KEY: UNSURE
<222> LOCATION: (30)..(30)
<223> OTHER INFORMATION: X indicates residue was not unambiguously
      identified
<220> FEATURE:
<221> NAME/KEY: UNSURE
<222> LOCATION: (37)..(37)
<223> OTHER INFORMATION: X indicates residue was not unambiguously
      identified
<220> FEATURE:
<221> NAME/KEY: UNSURE
<222> LOCATION: (39)..(39)
<223> OTHER INFORMATION: X indicates residue was not unambiguously
      identified

<400> SEQUENCE: 6

Lys Val Phe Asp Arg Xaa Glu Trp Ala Arg Val Leu Lys Ala Asn Gly
1               5                   10                  15

Met Asp Gly Tyr Arg Gly Ile Ser Leu Ala Asn Trp Val Xaa Leu Ser
            20                  25                  30

Lys Trp Glu Ser Xaa Tyr Xaa Thr
        35                  40

<210> SEQ ID NO 7
<211> LENGTH: 20
<212> TYPE: PRT
<213> ORGANISM: Macrozoarces americanus

<400> SEQUENCE: 7

Ser Gln Ser Val Val Ala Thr Tyr Leu Ile Pro Met Asn Thr Ala Leu
1               5                   10                  15

Thr Pro Ala Met
            20

<210> SEQ ID NO 8
<211> LENGTH: 17
<212> TYPE: PRT
<213> ORGANISM: Macrozoarces americanus

<400> SEQUENCE: 8

Asn Gln Ala Ser Val Val Ala Asn Gln Leu Ile Pro Ile Asn Thr Ala
1               5                   10                  15

Leu

<210> SEQ ID NO 9
<211> LENGTH: 23
<212> TYPE: PRT
```

-continued

```
<213> ORGANISM: Macrozoarces americanus

<400> SEQUENCE: 9

Asn Gln Ala Ser Val Val Ala Asn Gln Leu Ile Pro Ile Asn Thr Ala
1               5                   10                  15

Leu Thr Leu Val Met Met Arg
            20

<210> SEQ ID NO 10
<211> LENGTH: 16
<212> TYPE: PRT
<213> ORGANISM: Macrozoarces americanus

<400> SEQUENCE: 10

Ser Glu Val Val Thr Pro Val Gly Ile Pro Ala Glu Asp Ile Pro Arg
1               5                   10                  15

<210> SEQ ID NO 11
<211> LENGTH: 8
<212> TYPE: PRT
<213> ORGANISM: Macrozoarces americanus

<400> SEQUENCE: 11

Leu Val Ser Met Gln Val Asn Arg
1               5

<210> SEQ ID NO 12
<211> LENGTH: 14
<212> TYPE: PRT
<213> ORGANISM: Macrozoarces americanus

<400> SEQUENCE: 12

Ala Val Pro Leu Gly Thr Thr Leu Met Pro Asp Met Val Lys
1               5                   10

<210> SEQ ID NO 13
<211> LENGTH: 5
<212> TYPE: PRT
<213> ORGANISM: Macrozoarces americanus

<400> SEQUENCE: 13

Gly Tyr Pro Pro Ala
1               5

<210> SEQ ID NO 14
<211> LENGTH: 291
<212> TYPE: DNA
<213> ORGANISM: Artificial Sequence
<220> FEATURE:
<223> OTHER INFORMATION: clone AFP-III HPLC-12 invertase ss fusion;
      coding strand
<220> FEATURE:
<221> NAME/KEY: CDS
<222> LOCATION: (25)..(282)
<220> FEATURE:
<221> NAME/KEY: sig_peptide
<222> LOCATION: (25)..(84)
<220> FEATURE:
<221> NAME/KEY: mat_peptide
<222> LOCATION: (85)..()

<400> SEQUENCE: 14
catcacacaa acaaacaaaa caaa atg atg ctt ttg caa gcc ttc ctt ttc        51
                           Met Met Leu Leu Gln Ala Phe Leu Phe
                            -20                 -15 ctt ttg gct ggt ttt gca gcc aaa ata tct gct aat caa gcc tct gtt       99
```

```
                                                                                      -continued Leu Leu Ala Gly Phe Ala Ala Lys Ile Ser Ala Asn Gln Ala Ser Val
    -10              -5               -1   1              5 gtt gct aat caa ttg att cca ata aat act gct ttg act cta gtt atg         147
Val Ala Asn Gln Leu Ile Pro Ile Asn Thr Ala Leu Thr Leu Val Met
              10              15                      20 atg aga agt gaa gtt gtt act cca gtt ggt att cca gct gaa gat atc         195
Met Arg Ser Glu Val Val Thr Pro Val Gly Ile Pro Ala Glu Asp Ile
              25              30                      35 cct aga ctt gtt agt atg caa gtt aat aga gca gtt cct ttg ggt acc         243
Pro Arg Leu Val Ser Met Gln Val Asn Arg Ala Val Pro Leu Gly Thr
              40              45                      50 act ctt atg cca gat atg gtt aaa ggt tat cct cct gct tagtcttca           291
Thr Leu Met Pro Asp Met Val Lys Gly Tyr Pro Pro Ala
              55              60              65

<210> SEQ ID NO 15
<211> LENGTH: 86
<212> TYPE: PRT
<213> ORGANISM: Artificial Sequence
<220> FEATURE:
<223> OTHER INFORMATION: clone AFP-III HPLC-12 invertase ss fusion

<400> SEQUENCE: 15

Met Met Leu Leu Gln Ala Phe Leu Phe Leu Leu Ala Gly Phe Ala Ala
-20              -15                 -10              -5

Lys Ile Ser Ala Asn Gln Ala Ser Val Val Ala Asn Gln Leu Ile Pro
         -1   1              5                       10

Ile Asn Thr Ala Leu Thr Leu Val Met Met Arg Ser Glu Val Val Thr
              15              20                      25

Pro Val Gly Ile Pro Ala Glu Asp Ile Pro Arg Leu Val Ser Met Gln
         30              35                      40

Val Asn Arg Ala Val Pro Leu Gly Thr Thr Leu Met Pro Asp Met Val
45                  50              55                  60

Lys Gly Tyr Pro Pro Ala
                65

<210> SEQ ID NO 16
<211> LENGTH: 299
<212> TYPE: DNA
<213> ORGANISM: Artificial Sequence
<220> FEATURE:
<223> OTHER INFORMATION: clone AFP-III HPLC-12 invertase ss fusion;
      non-coding strand

<400> SEQUENCE: 16
agcttgaaga ctaagcagga ggataaacctt taaccatatc tggcataaga gtggtaccca     60
aaggaactgc tctattaact tgcatactaa caagtctagg gatatcttca gctggaatac    120
caactggagt aacaacttca cttctcatca taactagagt caaagcagta tttattggaa    180
tcaattgatt agcaacaaca gaggcttgat tagcagatat tttggctgca aaaccagcca    240
aaaggaaaag gaaggcttgc aaaagcatca ttttgttttg tttgtttgtg tgatgagct     299

<210> SEQ ID NO 17
<211> LENGTH: 63
<212> TYPE: PRT
<213> ORGANISM: Macrozoarces americanus

<400> SEQUENCE: 17

Gln Ser Val Val Ala Thr Gln Leu Ile Pro Ile Asn Thr Ala Leu Thr
1                5                  10                  15
```

```
Pro Ala Met Met Glu Gly Lys Val Thr Asn Pro Ile Gly Ile Pro Phe
            20                  25                  30

Ala Glu Met Ser Gln Ile Val Gly Lys Gln Val Asn Thr Pro Val Ala
            35                  40                  45

Lys Gly Gln Thr Ile Met Pro Asn Met Val Lys Thr Tyr Ala Ala
    50                  55                  60
```

<210> SEQ ID NO 18
<211> LENGTH: 64
<212> TYPE: PRT
<213> ORGANISM: Macrozoarces americanus

<400> SEQUENCE: 18

```
Gln Ser Val Val Ala Thr Gln Leu Ile Pro Ile Asn Thr Ala Leu Thr
1               5                   10                  15

Pro Ala Met Met Glu Gly Lys Val Thr Asn Pro Ile Gly Ile Pro Phe
            20                  25                  30

Ala Glu Met Ser Gln Ile Val Gly Lys Gln Val Asn Thr Pro Val Ala
            35                  40                  45

Lys Gly Gln Thr Ile Met Pro Asn Met Val Lys Thr Tyr Val Ala Gly
    50                  55                  60
```

<210> SEQ ID NO 19
<211> LENGTH: 64
<212> TYPE: PRT
<213> ORGANISM: Macrozoarces americanus

<400> SEQUENCE: 19

```
Ser Gln Ser Val Val Ala Thr Arg Leu Ile Pro Met Asn Thr Ala Leu
1               5                   10                  15

Thr Pro Ala Met Met Glu Gly Lys Val Thr Asn Pro Ile Gly Ile Pro
            20                  25                  30

Phe Ala Glu Met Ser Gln Ile Val Gly Lys Gln Val Asn Arg Ile Val
            35                  40                  45

Ala Lys Gly Gln Thr Leu Met Pro Asn Met Val Lys Thr Tyr Ala Ala
    50                  55                  60
```

<210> SEQ ID NO 20
<211> LENGTH: 64
<212> TYPE: PRT
<213> ORGANISM: Macrozoarces americanus

<400> SEQUENCE: 20

```
Ser Gln Ser Val Val Ala Thr Gln Leu Ile Pro Met Asn Thr Ala Leu
1               5                   10                  15

Thr Pro Ala Met Met Glu Gly Lys Val Thr Asn Pro Ile Gly Ile Pro
            20                  25                  30

Phe Ala Glu Met Ser Gln Ile Val Gly Lys Gln Val Asn Arg Ile Val
            35                  40                  45

Ala Lys Gly Gln Thr Leu Met Pro Asn Met Val Lys Thr Tyr Ala Ala
    50                  55                  60
```

<210> SEQ ID NO 21
<211> LENGTH: 62
<212> TYPE: PRT
<213> ORGANISM: Macrozoarces americanus

<400> SEQUENCE: 21

```
Ser Val Val Ala Thr Gln Leu Ile Pro Ile Asn Thr Ala Leu Thr Pro
1               5                   10                  15
```

```
Ala Met Met Glu Gly Lys Val Thr Asn Pro Ile Gly Ile Pro Phe Ala
            20                  25                  30

Glu Met Ser Gln Ile Val Gly Lys Gln Val Asn Arg Ile Val Ala Lys
            35                  40                  45

Gly Gln Thr Leu Met Pro Asn Met Val Lys Thr Tyr Ala Ala
    50                  55                  60
```

<210> SEQ ID NO 22
<211> LENGTH: 66
<212> TYPE: PRT
<213> ORGANISM: Macrozoarces americanus

<400> SEQUENCE: 22

```
Ser Gln Ser Val Val Ala Thr Gln Leu Ile Pro Met Asn Ser Ala Leu
1               5                   10                  15

Thr Pro Val Met Met Glu Gly Lys Val Thr Asn Pro Ile Gly Ile Pro
            20                  25                  30

Phe Ala Glu Met Ser Gln Val Val Gly Lys Gln Val Asn Arg Pro Val
            35                  40                  45

Ala Lys Gly Gln Thr Ile Met Pro Asn Met Val Lys Thr Tyr Ala Ala
    50                  55                  60

Gly Lys
65
```

<210> SEQ ID NO 23
<211> LENGTH: 66
<212> TYPE: PRT
<213> ORGANISM: Macrozoarces americanus

<400> SEQUENCE: 23

```
Ser Gln Ser Val Val Ala Thr Gln Leu Ile Pro Ile Asn Thr Ala Leu
1               5                   10                  15

Thr Pro Val Met Met Glu Gly Lys Val Thr Asn Pro Ile Gly Ile Pro
            20                  25                  30

Phe Ala Glu Met Ser Gln Ile Val Gly Lys Gln Val Asn Thr Pro Val
            35                  40                  45

Ala Lys Gly Gln Thr Ile Met Pro Asn Met Val Lys Thr Tyr Ala Ala
    50                  55                  60

Gly Lys
65
```

<210> SEQ ID NO 24
<211> LENGTH: 66
<212> TYPE: PRT
<213> ORGANISM: L. polaris

<400> SEQUENCE: 24

```
Ser Gln Ser Val Val Ala Thr Gln Leu Ile Pro Ile Asn Thr Ala Leu
1               5                   10                  15

Thr Pro Val Met Met Glu Gly Lys Val Thr Asn Pro Ile Gly Ile Pro
            20                  25                  30

Phe Ala Glu Met Ser Gln Ile Val Gly Lys Gln Val Asn Thr Pro Val
            35                  40                  45

Ala Lys Gly Gln Thr Leu Met Pro Asn Met Val Lys Thr Tyr Ala Ala
    50                  55                  60

Gly Lys
65
```

<210> SEQ ID NO 25
<211> LENGTH: 65
<212> TYPE: PRT
<213> ORGANISM: woolffish

<400> SEQUENCE: 25

Ser Gln Ser Val Val Ala Thr Gln Leu Ile Pro Ile Asn Thr Ala Leu
1               5                   10                  15

Thr Pro Ile Met Met Lys Gly Gln Val Val Asn Pro Ala Gly Ile Pro
            20                  25                  30

Phe Ala Glu Met Ser Gln Ile Val Gly Lys Gln Val Asn Arg Ala Val
        35                  40                  45

Ala Lys Asp Glu Thr Leu Met Pro Asn Met Val Lys Thr Tyr Arg Ala
    50                  55                  60

Ala
65

<210> SEQ ID NO 26
<211> LENGTH: 65
<212> TYPE: PRT
<213> ORGANISM: woolffish

<400> SEQUENCE: 26

Ser Gln Ser Val Val Ala Thr Gln Leu Ile Pro Ile Asn Thr Ala Leu
1               5                   10                  15

Thr Pro Ile Met Met Lys Gly Gln Val Val Asn Pro Ala Gly Ile Pro
            20                  25                  30

Phe Ala Glu Met Ser Gln Ile Val Gly Lys Gln Val Asn Arg Pro Val
        35                  40                  45

Ala Lys Asp Glu Thr Leu Met Pro Asn Met Val Lys Thr Tyr Arg Ala
    50                  55                  60

Ala
65

<210> SEQ ID NO 27
<211> LENGTH: 66
<212> TYPE: PRT
<213> ORGANISM: Macrozoarces americanus

<400> SEQUENCE: 27

Asn Gln Ala Ser Val Val Ala Asn Gln Leu Ile Pro Ile Asn Thr Ala
1               5                   10                  15

Leu Thr Leu Val Met Met Arg Ser Glu Val Val Thr Pro Val Gly Ile
            20                  25                  30

Pro Ala Glu Asp Ile Pro Arg Leu Val Ser Met Gln Val Asn Arg Ala
        35                  40                  45

Val Pro Leu Gly Thr Thr Leu Met Pro Asp Met Val Lys Gly Tyr Pro
    50                  55                  60

Pro Ala
65

<210> SEQ ID NO 28
<211> LENGTH: 69
<212> TYPE: PRT
<213> ORGANISM: Macrozoarces americanus

<400> SEQUENCE: 28

Asn Gln Ser Val Val Ala Asn Gln Leu Ile Pro Ile Asn Thr Ala Leu
1               5                   10                  15

```
Thr Leu Val Met Met Thr Thr Arg Val Ile Tyr Pro Thr Gly Ile Pro
            20                  25                  30

Ala Glu Asp Ile Pro Arg Leu Val Ser Met Gln Val Asn Gln Ala Val
            35                  40                  45

Pro Met Gly Thr Thr Leu Met Pro Asp Met Val Lys Phe Tyr Cys Leu
            50                  55                  60

Cys Ala Pro Leu Asn
65

<210> SEQ ID NO 29
<211> LENGTH: 66
<212> TYPE: PRT
<213> ORGANISM: Macrozoarces americanus

<400> SEQUENCE: 29

Asn Lys Ala Ser Val Val Ala Asn Gln Leu Ile Pro Ile Asn Thr Ala
1               5                   10                  15

Leu Thr Leu Val Met Met Arg Ala Glu Val Val Thr Pro Ala Gly Ile
            20                  25                  30

Pro Ala Glu Asp Ile Pro Arg Leu Val Gly Leu Gln Val Asn Arg Ala
            35                  40                  45

Val Leu Ile Gly Thr Thr Leu Met Pro Asp Met Val Lys Gly Tyr Ala
            50                  55                  60

Pro Gln
65

<210> SEQ ID NO 30
<211> LENGTH: 64
<212> TYPE: PRT
<213> ORGANISM: R. dearborni

<400> SEQUENCE: 30

Asn Lys Ala Ser Val Val Ala Asn Gln Leu Ile Pro Ile Asn Thr Ala
1               5                   10                  15

Leu Thr Leu Ile Met Met Lys Ala Glu Val Val Thr Pro Met Gly Ile
            20                  25                  30

Pro Ala Glu Asp Ile Pro Arg Ile Ile Gly Met Gln Val Asn Arg Ala
            35                  40                  45

Val Pro Leu Gly Thr Thr Leu Met Pro Asp Met Val Lys Asn Tyr Glu
            50                  55                  60

<210> SEQ ID NO 31
<211> LENGTH: 63
<212> TYPE: PRT
<213> ORGANISM: A. brachycephalus

<400> SEQUENCE: 31

Thr Lys Ser Val Val Ala Ser Gln Leu Ile Pro Ile Asn Thr Ala Leu
1               5                   10                  15

Thr Pro Ala Met Met Lys Ala Lys Glu Val Ser Pro Lys Gly Ile Pro
            20                  25                  30

Ala Glu Glu Met Ser Lys Ile Val Gly Met Gln Val Asn Arg Ala Val
            35                  40                  45

Asn Asp Leu Glu Thr Leu Met Pro Asp Met Val Lys Thr Tyr Gln
            50                  55                  60

<210> SEQ ID NO 32
<211> LENGTH: 63
```

```
<212> TYPE: PRT
<213> ORGANISM: A. brachycephalus

<400> SEQUENCE: 32

Thr Lys Ser Val Val Ala Asn Gln Leu Ile Pro Ile Asn Thr Ala Leu
1               5                   10                  15

Thr Leu Val Met Met Lys Ala Glu Glu Val Ser Pro Lys Gly Ile Pro
            20                  25                  30

Ala Glu Glu Ile Pro Arg Leu Val Gly Met Gln Val Asn Arg Ala Val
        35                  40                  45

Tyr Leu Asp Glu Thr Leu Met Pro Asp Met Val Lys Asn Tyr Glu
50                  55                  60
```